US007364900B2

(12) United States Patent
Black et al.

(10) Patent No.: US 7,364,900 B2
(45) Date of Patent: Apr. 29, 2008

(54) MULTI-LINEAGE DIRECTED INDUCTION OF BONE MARROW STROMAL CELL DIFFERENTIATION

(75) Inventors: Ira B. Black, Skillman, NJ (US); Dale Woodbury, Middletown, NJ (US)

(73) Assignee: University of Medicine and Dentistry of New Jersey, Somerset, NJ (US)

( * ) Notice: Subject to any disclaimer, the term of this patent is extended or adjusted under 35 U.S.C. 154(b) by 368 days.

(21) Appl. No.: 10/820,380

(22) Filed: Apr. 7, 2004

(65) Prior Publication Data

US 2005/0009181 A1    Jan. 13, 2005

Related U.S. Application Data

(63) Continuation of application No. 09/946,325, filed on Sep. 5, 2001, now abandoned.

(51) Int. Cl.
| | |
|---|---|
| *C12N 5/00* | (2006.01) |
| *C12N 5/02* | (2006.01) |
| *C12N 5/08* | (2006.01) |
| *C12N 5/06* | (2006.01) |
| *C12N 5/10* | (2006.01) |

(52) U.S. Cl. .................. 435/377; 435/372; 435/355
(58) Field of Classification Search ................ 435/377, 435/372, 355
See application file for complete search history.

(56) References Cited

U.S. PATENT DOCUMENTS 6,528,245 B2 *   3/2003   Sanchez-Ramos et al. ... 435/1.1

FOREIGN PATENT DOCUMENTS

| WO | WO 9956759 | 11/1999 |
|---|---|---|
| WO | WO 0159072 | 8/2001 |

OTHER PUBLICATIONS

Philippe, 1989, Journal of Clinical investigation, 84: 672-677.*
Odorico et al., 2001, Stem Cells, 19: 193-204.*
Thomas et al., 1999, Endocrinology, 140: 5036-5044.*
Woodbury et al., 2000, Journal of Neuroscience, 61: 364-370.*
Zaret, Kenneth S. "Hepatocyte differentiation : from the endoderm and beyond," *Current Opinion and Development*, 11:568-577 (2001).
Woodbury et al., "Adult Rat and Human Bone Marrow Stromal Cells Differentiate Into Neorons," *Journal of Neuroscience Research*, 61:364-370 (2000).
Sanchez-Ramos, J., et al., "Adult Bone Marrow Stromal Cells Differentiate into Nueral Cells In Vitro," *Experimental Neurology*, 164:247-256 (2000).

* cited by examiner

*Primary Examiner*—Anne Marie Wehbe'
*Assistant Examiner*—Joanne Hama
(74) *Attorney, Agent, or Firm*—Licata & Tyrrell PC

(57) ABSTRACT

Methods of inducing differentiation of mammalian bone marrow stromal cells into cells of multiple embryonic lineages by contacting marrow stromal cells with precursor differentiation-inducing compounds followed by contacting the partially differentiated precursor cells with specific cell type differentiation-inducing compounds. In one embodiment, the MSC derived precursor cell cultures comprise cells, at least some of which simultaneously express markers that are characteristic of endodermal and ectodermal cell types. In another embodiment, the differentiated cells are insulin-secreting pancreatic islet cells. Precursor differentiation-inducing compounds of the invention include anti-oxidants such as, but not limited to, beta-mercaptoethanol, dimethylsulfoxide, butylated hydroxyanisole, butylated hydroxytoluene, ascorbic acid, dimethylfumarate, and n-acetylcysteine. Endodermal cell differentiation-inducing compounds of the invention include but are not limited to anti-oxidants and growth factors including basic fibroblast growth factor. Once induced to differentiate into a particular cell type, the cells can be used for cell therapy, gene therapy, or both, for treatment of diseases, disorders, or conditions associated with tissues of multiple embryonic origins.

2 Claims, 10 Drawing Sheets

A

B

C

D

SEQUENCE LISTING

```
<160> NUMBER OF SEQ ID NOS: 22

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: nucleic
      acid primer

<400> SEQUENCE: 1
aggtggcctt cctgcggagc aatc                                          24

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: nucleic
      acid primer

<400> SEQUENCE: 2
gcctcaggag acttcacggg agac                                          24

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: nucleic
      acid primer

<400> SEQUENCE: 3
ggctttgaag cagcatggct gaac                                          24

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: nucleic
      acid primer

<400> SEQUENCE: 4
ggcctgatca caaaccctgc ttgg                                          24

<210> SEQ ID NO 5
<211> LENGTH: 23
<212> TYPE: DNA
<213> ORGANISM: Artificial Sequence
<220> FEATURE:
```

<223> OTHER INFORMATION: Description of Artificial Sequence: nucleic
      acid primer

<400> SEQUENCE: 5
tgaccaaatc atacagcgag agc                                           23

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: nucleic
      acid primer

<400> SEQUENCE: 6
agaagttgcc attgatgctg agcg                                          24

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: nucleic
      acid primer

<400> SEQUENCE: 7
gagacgtatc acctctgcac                                               20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: nucleic
      acid primer

<400> SEQUENCE: 8
ggaagcaacg tctgtgaggt                                               20

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: nucleic
      acid primer

<400> SEQUENCE: 9
ctacagttgc tccaacgttg ccagg                                         25

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: nucleic
      acid primer

<400> SEQUENCE: 10
agtaaccagc ttccaggcgt ttgg                                          24

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: nucleic acid primer

<400> SEQUENCE: 11
tctccttcca gtccacaaac gacc                                          24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: nucleic
      acid primer

<400> SEQUENCE: 12
cttccctttc taactgatga tctg                                          24

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: nucleic
      acid primer

<400> SEQUENCE: 13
actatggttc gctaccgaat gagg                                          24

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: nucleic
      acid primer

<400> SEQUENCE: 14
atcaacatgg aatggtgttg tggc                                          24

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: nucleic
      acid primer

<400> SEQUENCE: 15
ttggactgag ctactgtctg ttgc                                          24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: nucleic
      acid primer

<400> SEQUENCE: 16
tttcagcaca cagcgccatt tggc                                          24

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: nucleic
      acid primer

```
<400> SEQUENCE: 17
ctcagagaac cctgtggatg tccg                                           24

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: nucleic
      acid primer

<400> SEQUENCE: 18
gcatctcgct ccaggtattt gtagg                                          25

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: nucleic
      acid primer

<400> SEQUENCE: 19
agtttcttgg tctctgggga cagc                                           24

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: nucleic
      acid primer

<400> SEQUENCE: 20
aactgatggt caggatcgac aggg                                           24

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: nucleic
      acid primer

<400> SEQUENCE: 21
cttcaacagc atcatccaga catc                                           24

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: nucleic
      acid primer

<400> SEQUENCE: 22
caccttggtc gtggatcatc atagc                                          25
```

MULTI-LINEAGE DIRECTED INDUCTION OF BONE MARROW STROMAL CELL DIFFERENTIATION

This application is a continuation of U.S. Ser. No. 09/946,325 filed Sep. 5, 2001, now abandoned which is herein incorporated by reference in its entirety.

BACKGROUND OF THE INVENTION

Pluripotent stem cells have been detected in multiple tissues in the adult mammal, participating in normal replacement and repair, while undergoing self-renewal (Hay, 1966, Regeneration, Holt, Rinehart and Winston, New York; McKay, 1999, Nature Med. 5:261-262; Lemiscka, 1999, Ann. N.Y. Acad. Sci. 872:274-288; Owens and Friedenstein, 1988, Ciba Foundation Syp. 136, Chichester, U.K. pp. 42-60; Prockop, 1997, Science 276:71-74; Ferrari et al., 1998, Science 279:1528-1530; Caplan, 1991, J. Orthop. Res. 9:641-650; Pereira et al., 1995, Proc. Natl. Acad. Sci. USA 92:4857-4861; Kuznetsov et al., 1997, Brit. J. Haemotology 97:561-570; Majumdar et al., 1998, J. Cell Physiol. 176:57-66; Pittenger et al., 1999, Science 284:143-147). A subclass of bone marrow stem cells is one prototype, capable of differentiating into osteogenic, chondrogenic, adipogenic and other mesenchymal lineages in vitro (Owens and Friedenstein, 20 1988, Ciba Foundation Symp. 136, Chichester, U.K. pp. 42-60; Prockop, 1997, Science 276; 71-74; Ferrari et al., 1998, Science 279:1528-1530; Caplan, 1991, J. Orthop. Res. 9:641-650; Pereira et al., 1995, Proc. Natl. Acad. Sci. USA 92:4857-4861; Kuznetsov et al., 1997, Brit. J. Haemotology 97:561-570; Majumdar et al., 1998, J. Cell. Physiol. 176:57-66; Pittenger et al., 1999, Science 284:143-147). These pluripotent cells have been termed marrow stromal cells (MSCs), and have been used clinically to treat osteogenesis imperfecta (Horwitz et al., 1999, Nature Med. 5:309-313).

The discovery of stem cell populations in the central nervous system (CNS) has generated intense interest, since the brain has long been regarded as incapable of regeneration (Reynolds and Weiss, 1992, Science 255:1707-1710; Richards et al., 1992, Proc. Natl. Acad. Sci. USA 89:8591-8595; Morshead et al., 1994, Neuron 13:1071-1082). Neural stem cells (NSCs) are capable of undergoing expansion and differentiating into neurons, astrocytes and oligodendrocytes in vitro (Reynolds and Weiss, 1992, Science 255:1707-1710; Johansson et al., 1999, Cell 96:25-34; Gage et al., 1995, Annu. Rev. Neurosci. 18:159-192; Vescovi et al., 1993, Neuron 11:951-966). The recent report demonstrating that NSCs can generate hematopoietic cells in vivo suggests that stem cell populations may be less restricted than previously thought (Bjornson, 1999, Science 283:534-537).

Adult MSC cells are both self-renewing and multipotential (Owens and Friedenstein, 1988, Ciba Foundation Symp. 136, Chichester, U.K. pp. 42-60; Prockop, 1997, Science 276; 71-74; Ferrari et al., 1998, Science 279: 1528-1530; Caplan,1991, J. Orthop. Res. 9:641-650; Pereira et al., 1995, Proc. Natl. Acad. Sci. USA 92:4857-4861; Kuznetsov et al., 1997, Brit. J. Haemotology 97:561-570; Majumdar et al., 1998, J. Cell. Physiol. 176:57-66; Pittenger et al., 1999, Science 284:143-147; Sanchez Ramos et al. Exp. Neurol. 2000 164(2) 247-56), thereby fulfilling many of the criteria of a stem cell population.

Recent studies show that neural stem cells have broad developmental potential, contributing to the development of blood as well as to all germ layers in chimeric embryos (Clarke, D. L. et al., Science (2000) 288: 1660-1663). During early embryonic development of mammalian embryos, developing neural cells share features with developing islet cells. A specific characteristic of neural precursor cells is their expression of the protein nestin (U. Lendhal, L. D. Zimmerman, R. D. McKay Cell: 23, 585 (1990) as described in U.S. Pat. No. 5,338,839. Recently, researchers have found the stem cell marker nestin within developing islet cells (H. Zulewski et al., 2001, Diabetes 50: 521) and others report the differentiation of nestin-positive embryonic stem cells to insulin-secreting structures similar to pancreatic islets in mice (N. Lumelsky et al. supra) and humans (Assady et al., Diabetes 50, August 2001). However, differentiation of insulin-secreting islet-type cells from adult stem cells has not previously been demonstrated. Common mechanisms of control and shared nestin expression point to a close relationship between pancreatic and neural progenitors which give rise to tissues of endodermal and ectodermal embryonic origin respectively.

We have recently demonstrated that MSCs can be induced to differentiate into neuronal cells (D. Woodbury et al., 2000, J. Neur. Sci. Res. 61, 364). Differentiation of MSCs into astrocytes and glial cells (WO 99/43286) has also been demonstrated. These recent studies indicate that rat and human MSCs are capable of differentiating into non-mesenchymal derivatives, suggesting that intrinsic genomic mechanisms of commitment, lineage restriction and cell fate are mutable. Environmental signals apparently can elicit the expression of pluripotentiality that extends well beyond the accepted fate restrictions of cells originating in classical embryonic germ layers.

To define the process of stem cell differentiation and elucidate underlying mechanisms, we have characterized MSCs and developing neurons more extensively, defining expression patterns for representative genes of different lineages and correlating expression with morphologic maturation. Our observations indicate that the "undifferentiated" MSCs express germline, endodermal and ectodermal genes, as well as the expected mesodermal genes. Neuronal differentiation of the MSCs involves complex modulation of these different gene sets, rather than simple on-off switching of neural and non-neural genes. We now describe, for the first time, conditions which permit the growth and expansion of endodermal cells, particularly insulin-producing pancreatic islet cells, differentiated from adult bone marrow stromal cells (MSCs). MSCs constitute a novel source of pancreatic islet cells and represent the only adult cells used for this purpose.

A number of disease states are associated with organs of endodermal lineage which include the liver, stomach, intestine, pancreas, and other endocrine glands. Type 1 and Type 2 diabetes and chronic pancreatitis result from the anatomical and functional loss of insulin-producing beta cells and the ductal and acinar cells, respectively, while uncontrolled proliferation of the ductal cells leads to pancreatic carcinogenesis. The replacement of these cells through regeneration or transplantation could offer lifelong treatment for diabetics and for patients with chronic pancreatitis. However, a major problem in implementing treatment is the lack of sufficient pancreatic/islet cell tissue for transplantation. The present invention officers the potential of generating sizable quantities of insulin-producing cells from adult bone marrow stromal cells.

Gut malignancies and inflammatory bowel diseases are major causes of morbidity and mortality. The cell differentiation techniques disclosed herein may be utilized to gain new insights about initiation, progression and treatment of tumorigenesis and offer new strategies to increase the absorptive function of the intestine.

Liver transplantation is the treatment of choice for many liver diseases. Unfortunately, the supply of donor organs is limiting and therefore many patients cannot benefit from this therapy. Therapeutic liver re-population with bone marrow derived cells holds the hope of overcoming the shortage in donor livers.

Despite the crucial need for obtaining endodermal cells for treatment a number of diseases, disorders, and conditions, associated with tissues of endodermal lineage, no method has previously been available for obtaining large numbers of endodermal cells without encountering the technical and ethical hurdles involved in obtaining adult human or fetal tissue. The present invention overcomes that need, offering the potential of generating sizable quantities of endodermal tissue from adult bone marrow stromal cells.

While previous studies have demonstrated that intrinsic genomic mechanisms of commitment, lineage restriction and mesenchymal cell fate of MSCs are mutable, it was unexpected that these adult cells could be induced to differentiate to cells associated with tissues of endodermal lineage including the liver, stomach, intestine, pancreas, and other endocrine glands.

SUMMARY OF THE INVENTION

In one aspect of the invention, a cell culture is provided that comprises cells, at least some of which simultaneously express polypeptide or mRNA markers that are characteristic of at least ectodermal and endodermal cells. Useful ectodermal markers include but are not limited to nestin, tau, neuron specific enolase, glial fibrillary acidic protein, especially nestin. Useful endodermal markers include but are not limited to ceruloplasmin.

According to another aspect of the invention, at least some cells of the culture simultaneously express the neuronal marker nestin and an endodermal marker, such as ceruloplasmin.

According to another aspect of the invention there is provided a method of producing a nestin-positive endodermal/neuronal precursor cell capable of differentiation into cells of at least endodermal or ectodermal lineage.

The present invention includes a method of inducing differentiation of an isolated marrow stromal cell into an endodermal cell, particularly a pancreatic islet cell. The method comprises contacting the isolated marrow stromal cell with at least one endodermal/neuronal precursor differentiation-inducing compound thereby producing a nestin-positive endodermal/neuronal precursor cell. The endodermal/neuronal precursor cell is contacted with at least one endodermal differentiating inducing compound, particularly an insulin-secreting pancreatic islet differentiation-inducing compound. This induces differentiation of the isolated marrow stromal cell into an endodermal cell, particularly an insulin-secreting pancreatic islet cell. In one embodiment, the at least one insulin-secreting pancreatic islet differentiation-inducing compound comprises a defined insulin secreting pancreatic islet differentiation-inducing medium.

In one aspect, the isolated marrow stromal cell is a rat cell. Preferably, the isolated marrow stromal cell is a human cell.

In one aspect, the nestin-positive pancreatic/neuronal precursor differentiation-inducing compound is an anti-oxidant. In another aspect, the anti-oxidant is selected from the group consisting of beta-mercaptoethanol, dimethylsulfoxide, butylated hydroxytoluene, butylated hydroxyanisole, ascorbic acid, dimethylfumarate, and n-acetylcysteine. In one aspect, the pancreatic islet differentiation-inducing compound is an anti-oxidant. In another aspect, the anti-oxidant is selected from the group consisting of beta-mercaptoethanol and butylated hydroxyanisole. In yet another aspect, the pancreatic differentiation-inducing anti-oxidant is beta-mercaptoethanol. In another aspect, the pancreatic islet differentiation-inducing anti-oxidant is butylated hydroxyanisole.

The pancreatic islet cell differentiation-inducing compound is also a growth factor in another aspect.

In a preferred aspect, the growth factor is basic fibroblast growth factor.

The invention further includes a method of producing an isolated insulin-secreting pancreatic islet cell. The method comprises isolating a marrow stromal cell, contacting the marrow stromal cell with at least one endodermal/neuronal precursor differentiation-inducing compound that differentiates the marrow stromal cell into a nestin-positive endodermal/neuronal precursor cell and contacting the nestin-positive endodermal/neuronal precursor cell with at least one differentiation-inducing compound that induces the nestin-positive precursor cell to differentiate into an isolated pancreatic islet cell, thereby producing an isolated pancreatic islet cell.

According to another aspect of the invention there is provided a method of producing an isolated nestin-positive endodermal/neuronal precursor cell capable of differentiating into an insulin producing pancreatic islet cell. The method comprises isolating a marrow stromal cell and contacting a isolated marrow stromal cell with at least one endodermal/neuronal precursor differentiation-inducing compound thereby producing an isolated nestin-positive endodermal/neuronal precursor cell capable of differentiating into an isolated insulin producing pancreatic islet cell To induce insulin producing pancreatic islet cell differentiation, the isolated endodermal/neuronal precursor cell is contacted with at least one insulin-secreting pancreatic islet differentiation-inducing compound. This induces differentiation of the isolated endodermal/neuronal precursor cell into an isolated insulin-secreting pancreatic islet cell.

The invention further includes a method of producing an isolated endodermal cell. The method comprises isolating a marrow stromal cell, contacting the marrow stromal cell with at least one endodermal/neuronal differentiation-inducing compound that partially differentiates the marrow stromal cell into a nestin-positive precursor cell and contacting the nestin-positive endodermal/neuronal precursor cell with at least one endodermal differentiation-inducing compound that induces the endodermal/neuronal precursor cell to differentiate into an isolated endodermal cell, thereby producing an isolated endodermal cell.

In addition, the invention includes a method of treating a human patient having a disease, disorder or condition associated with tissues of endodermal origin, particularly of pancreatic origin. The method comprises obtaining a bone marrow sample from a human donor, isolating stromal cells from the bone marrow sample, inducing the stromal cells to differentiate into nestin-positive endodermal/neuronal precursor cells and inducing the nestin-positive endodermal/neuronal precursor cells to differentiate into isolated endodermal cells, particularly insulin-secreting pancreatic islet cells, and administering the isolated endodermal cells to the body of the human patient. The presence of the isolated endodermal cells, particularly insulin-secreting pancreatic islet cells, in the body of the human patient effects treatment of the disease, disorder or condition of endodermal origin, particularly pancreatic origin.

In one aspect, the disease, disorder or condition associated with a tissue of endodermal origin is selected from the group consisting of Type I diabetes, Type II diabetes, pancreatitis, inflammatory bowel disease, stomach cancer, colon cancer, colo-rectal cancer and liver disease.

In another aspect, prior to administering the isolated endodermal cells, particularly insulin-secreting pancreatic islet cells, the isolated endodermal cells are transfected with an isolated nucleic acid encoding a therapeutic protein or peptide, particularly insulin wherein, when the protein or peptide is expressed in the cells, the protein or peptide serves to effect treatment of the disease, disorder or condition.

In an altern factor, an antibody, and a tumor toxic protein.

The present invention further includes a method of treating a human patient in need of endodermal cells, particularly insulin-secreting pancreatic islet cells. The method comprises obtaining marrow stromal cells from a human patient, propagating the marrow stromal cells in culture under conditions that induce their differentiation, inducing the stromal cells to differentiate into nestin-positive endodermal/neuronal precursor cells, inducing the nestin-positive endodermal/neuronal precursor cells to differentiate into isolated endodermal cells, particularly insulin-secreting pancreatic islet cells, transplanting the endodermal cells into the human patient in need of the endodermal cells, thereby treating the human patient in need of endodermal cells.

A preferred embodiment of the invention includes an isolated endodermal cell, particularly an insulin-secreting pancreatic islet cell, transfected with a therapeutic protein or peptide. The endodermal cell is isolated by the method of inducing differentiation of an isolated marrow cell into an endodermal cell, particularly an insulin-secreting pancreatic islet cell, as recited above. The endodermal cell is then transfected with an isolated nucleic acid encoding a therapeutic protein or peptide that, when expressed, will effect treatment of a disease, disorder, or condition associated with a tissue of endodermal origin, particularly pancreatic origin. In an aspect of the invention, the therapeutic protein or peptide encoded by the isolated nucleic acid is a cytokine, a chemokine, insulin, glucagon, another endocrine hormone, a trophic protein, a growth factor, an antibody, or a tumor toxic protein. The invention encompasses diseases, disorders, or conditions of organ systems of endodermal lineage including, but not limited to, Type I diabetes, Type II diabetes, pancreatitis, inflammatory bowel disease, stomach cancer, colon cancer, colo-rectal cancer and liver disease.

In one aspect, the transfected endodermal cell, particularly an insulin-secreting pancreatic islet cell, made by this method is a rodent cell. In another aspect the transfected endodermal cell is a rat cell. In a preferred aspect, the transfected cell made by this method is a human cell.

The invention also includes endodermal cells, particularly insulin-secreting pancreatic islet cells, made by the method of inducing differentiation of isolated marrow cells into nestin-positive endodermal/neuronal precursor cells and inducing the nestin-positive endodermal/neuronal precursor cells into endodermal cells, particularly insulin-secreting pancreatic islet cells. The method comprises contacting the isolated marrow stromal cells with at least one differentiation-inducing compound which induces the isolated marrow cells to differentiate to nestin-positive endodermal/neuronal precursor cells. Contact between the nestin-positive endodermal/neuronal precursor cells and at least one endodermal differentiation-inducing compound, in particular an insulin-secreting pancreatic islet cell inducing compound, induces differentiation of the nestin-positive endodermal/neuronal precursor cells into the endodermal cells of the invention, particularly insulin-secreting pancreatic islet cells.

In an aspect, the endodermal cells, particularly insulin-secreting pancreatic islet cells, made by this method are rodent cells. In another aspect, the endodermal cells, particularly insulin-secreting pancreatic islet cells, are rat cells. In a preferred aspect, the endodermal cells, particularly insulin-secreting pancreatic islet cells, made by this method are human cells.

The invention also includes an isolated endodermal cell, particularly an insulin-secreting pancreatic islet cell, produced by a method comprising isolating a marrow stromal cell and contacting the isolated marrow stromal cell with at least one endodermal/neuronal precursor differentiation-inducing compound that induces the isolated marrow stromal cell to differentiate into an isolated nestin-positive endodermal/neuronal precursor cell. The nestin-positive endodermal/neuronal precursor cell is contacted with at least one endodermal differentiation-inducing compound. This induces the isolated nestin-positive endodermla/neuronal precursor cell to differentiate into an isolated endodermal cell, particularly an insulin-secreting pancreatic islet cell The invention also includes an isolated transfected endodermal cell, particularly an insulin-secreting pancreatic islet cell, produced by a method comprising inducing differentiation of an isolated marrow cell into an endodermal cell, particularly an insulin-secreting pancreatic islet cell, as recited above. The endodermal cell is then transfected with an isolated nucleic acid encoding a therapeutic protein or peptide that, when expressed, will effect treatment of a disease, disorder, or condition associated with a tissue of endodermal origin, particularly pancreatic origin. In an aspect of the invention, the therapeutic protein or peptide encoded by the isolated nucleic acid is a cytokine, a chemokine, insulin, glucagon, another endocrine hormone, a trophic protein, a growth factor, an antibody, or a tumor toxic protein.

In an aspect, the transfected endodermal cell is rodent cell. In another aspect, the transfected endodermal cell is a rat cell. In a preferred aspect, the transfected endodermal cell is a human cell.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiment(s) which are presently preferred. It should be understood, however, that the invention is not limited to the precise arrangements and instrumentalities shown.

Neuronal induction decreased expression of ceruloplasmin, NMDA receptor glutamate binding subunit, and protamine2 significantly, while expression of aldolase C, SM22α and syntaxin was less affected. The level of expression of APP was not changed by neuronal induction. λ/Hind III DNA was used as M. W. marker (M).

Figure 3A:
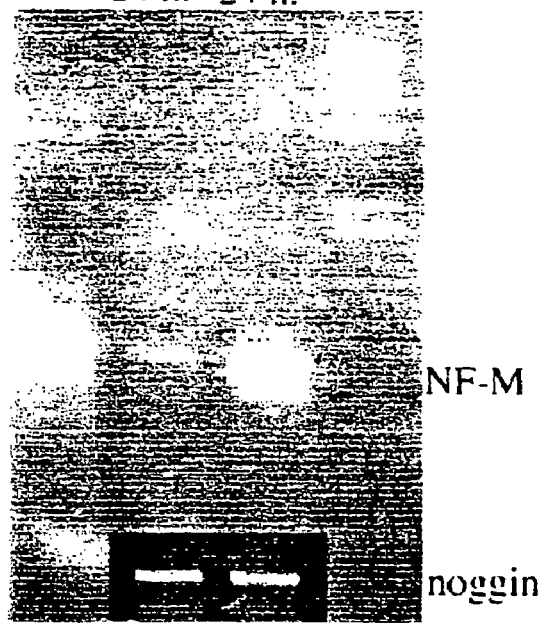
Figure 3B:
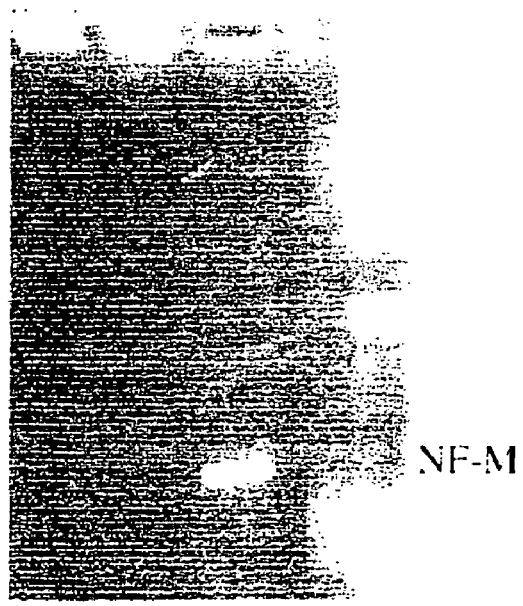

FIG. 3A-B. MSC-derived neurons express the neuronal marker NF-M. A. RNA was harvested from undifferentiated MSCs maintained in SFM (SFM) and from MSCderived neurons maintained in NIM (NIM) for 24 hours. RT-PCR performed with primers specific for NF-M yielded a single band from MSC-derived neurons. A very faint band corresponding to the NF-M product was also detected in cells maintained in SFM. RT-PCR of RNA derived from the cerebellum of adult rats yielded a NF-M product of the same size, demonstrating specificity of the reaction. Equal amplification of noggin (inset) indicates equivalence of cDNA target. λ/Hind III DNA was used as M.W. marker (M). B. NF-M message was undetectable in MSCs maintained in SFM, but is just above the level of detection in cells exposed to NIM at 5 hours. The level of expression of NF-M increased dramatically after a 24-hour exposure to NIM. λ/Hind III DNA was used as M. W. marker (M).

FIG. 4 A-B. Neuronal differentiation alters expression of neural genes. A. RT-PCR analysis was utilized to assess expression of neuroglial genes during the initial 48 hours of neuronal differentiation. APP expression in undifferentiated MSCs (S), MSC-derived neurons at 24 hours (N-24) and 48 hours (N-48) post-induction remained constant. GFAP and NeuroD (NeD) mRNA levels were elevated in MSCs and decreased as neuronal differentiation proceeded. Message for the neuronal markers NF-M and tau were undetectable in MSCs but increased with ongoing neuronal differentiation. tau message was present in multiple isoforms (bracketed bands). λ/Hind III DNA was used as M. W. marker (M). B. RT-PCR followed by high resolution electrophoresis revealed three distinct bands corresponding to known splice variants of tau message that were present in MSC-derived neurons at 48 hours post-induction (<). No signal was discernible in undifferentiated MSCs. Sizes (bp) of low M. W. fragments of Kilobase ladder (Kb) are indicated.

FIG. 5 A-B. MSC-derived neurons express tau 10 days after induction. MSC-derived neurons were fixed and processed immunocytochemically for tau expression. A. Intensely tau-positive neuron (<) displays contracted cell body and long processes studded with varicosity-like swellings (arrows) while neighboring cells lack both neuronal morphologies and strong tau staining. B. tau-positive MSC-derived neuron (>) exhibits an extremely long process which terminates in a growth conelike structure (arrow). Neighboring cells show varying intensities of tau staining indicative of heterogeneous level of expression of this neuronal marker. Magnification 200×.

FIG. 6 A-D. MSC-derived neurons express TOAD-64, β-tubulin III and synaptophysin. MSC-derived neurons were fixed 10 days after differentiation and processed immunocytochemically for neuronal markers. MSC-derived neurons express (A) TOAD-64, (B) β-tubulin III, and (C) synaptophysin, with intense staining in the varicosity-like swellings (arrows). Magnification 200×. D. RTPCR for synaptophysin was performed on RNA harvested from undifferentiated MSCs (S) and MSC-derived neurons 24 (N-24) and 48 (N-48) hours postinduction. A signal indicating the presence of synaptophysin message is not detected in MSCs, but becomes increasingly evident with progressing neuronal differentiation.

FIG. 7 A-D. MSC-derived neurons express enzymes required for neurotransmitter biosynthesis. MSC-derived neurons were fixed at 10 days post-induction and processed immunocytochemically. A, B. Cells exhibiting neuronal morphologies show intense staining for ChAT (>), while flat stromal-like cells (arrow) do not. The perinuclear staining pattern is particularly evident in the bipolar neuron in A. C, D. A subpopulation of cells express TH (>), while the majority of MSC-derived neurons (arrow) do not express this protein. Magnification 200×.

FIG. 8 A-C. Neuronal differentiation is reversible morphologically and transcriptionally. A. MSC-derived neurons at 24 hours post induction display neuronal morphologies with highly refractile cell bodies and long process like extensions. B. Same cells as in A. 24 hours after NIM withdrawn. Cell bodies have flattened and processes have been withdrawn, yielding cells with stromal morphologies. Magnification 200×. C. Morphologic reversion is accompanied by changes in gene expression, identified by RT-PCR. Ceruloplasmin, protamine2, GFAP, and NeuroD are expressed at higher levels in reverted cells (R48) than in MSC-derived neurons (N-48) at 48 hours post-induction. The level of expression of APP and SM22cc is unaltered by the reversion process.

Figure 9A:
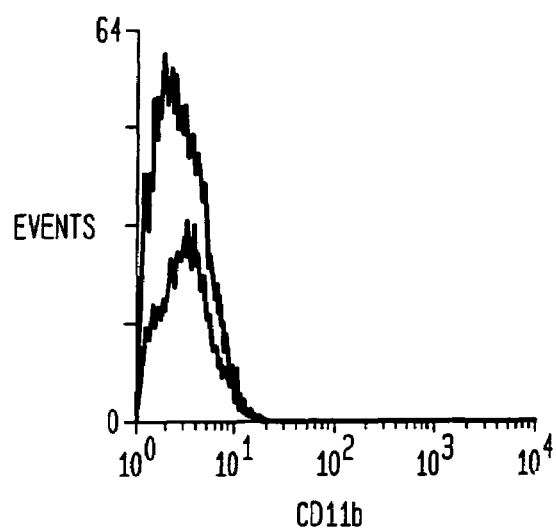

FIG. 9A is a graph depicting fluorescent cell sorting of passage 1 rMSCs using mouse monoclonal antibodies that specifically bind with cell surface marker CD11b (CD11/integrin alpham/Mac-1 alpha chain; Pharmingen, San Diego, Calif.) (unfilled peaks). The secondary antibody used was anti-mouse antibody conjugated with fluoresceine isothiocyanate (FITC). An isotype control is included in each experiment to identify background fluorescence (filled peaks). Number of cells analyzed (Events) is plotted on the Y-axis, while intensity of staining is plotted on the X-axis.

Figure 9B:
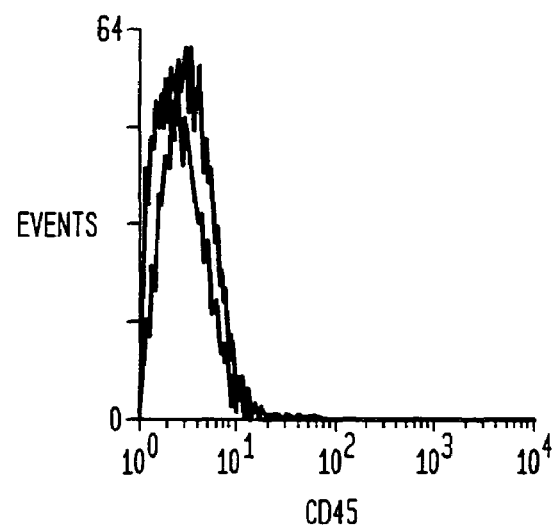

FIG. 9B is a graph depicting fluorescent cell sorting of passage 1 rMSCs using mouse monoclonal antibodies that specifically bind with cell surface marker CD45/leukocyte common antigen (Pharmingen) (unfilled peaks). The secondary antibody is anti-mouse antibody conjugated with fluoresceine isothiocyanate (FITC). An isotype control is included in each experiment to identify background fluorescence (filled peaks). Number of cells analyzed (Events) is plotted on the Y-axis, while intensity of staining is plotted on the X-axis.

Figure 9C:
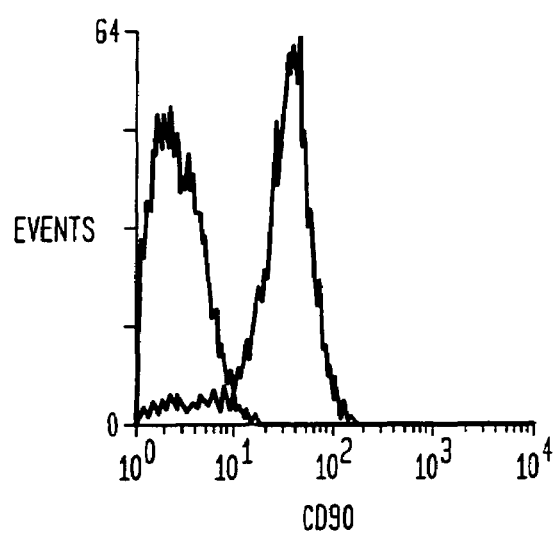

FIG. 9C is a graph depicting fluorescent cell sorting of passage 1 rMSCs using mouse monoclonal antibodies that specifically bind with cell surface marker CD90/Thy-1/CD90.1/Thy1.1 (Pharmingen) (unfilled peaks). The secondary antibody is anti-mouse antibody conjugated with fluoresceine isothiocyanate (FITC). An isotype control is included in each experiment to identify background fluorescence (filled peaks). Number of cells analyzed (Events) is plotted on the Y-axis, while intensity of staining is plotted on the X-axis. The data disclosed herein demonstrate that the fluorescence intensity is greater (shifted to the right) when rMSCs are incubated with CD90 antibody (unfilled), as compared to control antibody (filled), indicating that the vast majority of cells in the rMSC cultures express CD90, consistent with their undifferentiated state.

DETAILED DESCRIPTION OF THE INVENTION

The novel methods of the subject invention are based on the discovery MSC stem cells, which we have previously shown to be capable of differentiating into neuronal cells, express germline, ectodermal, endodermal and mesodermal genes prior to neurogenesis. (Woodbury, et al.—submitted for publication). That is, MSCs are not undifferentiated but rather "multi-differentiated." The expression of genes characteristic of the endoderm, e.g. ceruloplasmin, by MSCs prior to neurogenesis was unexpected and MSCs represent the first adult stem cells used for the purpose of generating cells of endodermal lineage.

According to the present invention, marrow stromal cells are contacted with at least one endodermal/neuronal differentiation-inducing agent that mediates partial differentiation of the cells into precursor cells which express the specific marker nestin. The nestin-positive precursor cells prepared according to the methods described herein have the potential to differentiate into cells of neuronal and/or endodermal lineage.

MSC-cultures simultaneously express a wide array of mRNA and protein markers that are normally associated with cells of multiple distinct developmental lineages including neural (ectodermal), vascular/hematopoietic (mesodermal), muscle (mesodermal) and endoderm lineages. Mesodermal cells include, for example, connective tissue cells, (e.g. fibroblasts), bone, cartilage (e.g. chondrocytes), muscle (e.g. myocytes), blood and vessels, lymphatic and lymphoid organ cells, pleura, pericardium, kidney, gonad and peritoneum. Ectodermal cells include, for example, epidermal cells such as those of the nail, hair, glands of the skin, nervous system, external organs (e.g. eyes and ears) and the mucosal membranes (e.g. mouth, nose, anal, vaginal). Endodermal cells include, for example, those of the pharynx, respiratory tract, digestive tracts, bladder, liver, pancreas, and urethra.

The untreated MSC cultures of the invention simultaneously express an unexpectedly wide variety of mRNA and polypeptide lineage markers in a pattern different from naturally occurring differentiated cells. Thus, the MSC cell cultures of the invention can be characterized by the presence or absence of the markers. Such markers include, for example, the endodermal marker ceruloplasmin, the mesodermal marker SM22α, the germline marker protamine and ectodermal aldolase C, amyloid precursor protein, NMDA, glutamate binding subunit and syn-taxin. In the mixed culture, not all markers will be present in all cells, e.g. some markers may be absent due to differences in developmental state, culture conditions, etc. All cultures contacted with the endodermal/neuronal precursor-inducing compound of the invention will express the ectodermal marker nestin and at least one marker characteristic of endodermal lineage e.g. ceruloplasmin.

Expression of markers from different lineages in the resulting cultures can be due to multiple cell types within the culture or can result from a multi- or pluri-potent cell capable of many distinct patterns of expression and physiological roles. Clonal lines may be isolated and RT-PCR expression profile carried out on each. Expression of a wide variety of lineages within clonal lines indicates that differentiated cells are derived from a multi-potent cell. The unique, multifarious expression characteristics of MSCs suggest a multifunctional, multipotential differentiation capability.

Growth media can be enhanced with a wide variety of compounds including but not limited to retinoic acid, dimethylsulfoxide (DMSO), cAMP activators such as forskolin, isobutylmethylxanthine and dibutyryl cAMP, antioxidants such as beta-mercaptoethanol, dimethylsulfoxide, butylated hydroxytoluene, butylated hydroxyanisole, ascorbic acid, dimethylfumarate, N-acetylcysteine and cytokines such as basic fibroblast growth factor, epidermal growth factor, and nerve growth factor.

The nestin-positive precursor cells prepared according to the methods described herein have the potential to differentiate into cells of neuronal and/or endodermal lineage, particularly pancreatic lineage, and may further be genetically modified. Thus, the cell differentiation methods disclosed herein provide entirely new strategies for repairing or replacing damaged or diseased tissues associated with organs of endodermal lineage such as the liver, stomach, intestine pancreas and other endocrine glands.

The invention includes a method of inducing isolated marrow stromal cells to differentiate into endodermal cells, in particular, pancreatic islet cells. Generally, cells are isolated from a donor, stromal cells are obtained therefrom, usually using a cell-sorting method, and the stromal cells are subsequently cultured in vitro. The donor may be a rat, for example, or the donor may be a human. The invention is intended to encompass a mammalian donor and should not be limited to the specific donors disclosed herein.

Induction of Endodermal/Precursor Cells

In one embodiment, to induce partial differentiation of at least some of the undifferentiated MSCs to endodermal/neuronal precursor cells, the undifferentiated MSCs are pre-treated with an effective amount of at least one endodermal/neuronal precursor-inducing compound which is introduced into the cell culture for a period of time. The length of time may vary according to the precise method being contemplated and should not be construed as limiting the invention in any way. After pre-treatment exposure to the endodermal/neural precursor-inducing compound, the cells are transferred to a serum-free medium containing an effective amount of the same endodermal/neuronal precursor-inducing compound resulting in partial differentiation of the marrow stromal cells to nestin-positive endodermal/neural precursor cells.

In preferred embodiments of the invention, antioxidants serve as the endodermal/neuronal precursor-inducing compounds, including but not limited to β-mercaptoethanol, dimethylsulfoxide, butylated hydroxytoluene, butylated hydroxyanisole, ascorbic acid, dimethylfumarate, and n-acetylcysteine. Particularly preferred is β-mercaptoethanol. Antioxidants as used herein should be construed to include all antioxidants, as well as other compounds which induce the proliferation of nestin-positive MSCs.

Cell cultures and clonal lines of the nestin positive precursor cells of the invention retain a broad pattern of gene expression including simultaneous expression of markers normally associated with cells of the neural and endodermal lineages. For example the simultaneous expression of the neuronal marker nestin and the endodermal marker ceruloplasmin as detected by reverse transcriptase polymerase chain reaction (RT-PCR) confirms that these nestin-positive cells are indeed multi-potent precursor cells capable of differentiating into cells of ectodermal and endodermal lineage.

Induction of Pancreatic Phenotype

To induce the insulin-secreting pancreatic islet phenotype from adult stem cells according to one embodiment of the present invention, MSCs are pre-treated with an effective amount of at least one endodermal/neuronal precursor-inducing compound that is introduced into the cell culture for a period of time. The length of time may vary according to the precise method being contemplated and should not be construed as limiting the invention in any way. After pre-treatment exposure to the at least one endodermal/neuronal precursor differentiation-inducing compound, the cells are transferred to a serum-free medium containing an amount of the same endodermal/neuronal precursor-inducing compound to provide an environment that promotes vigorous proliferation of nestin-positive endodermal/neuronal precursor cells. Nestin-positive precursor cells are then transferred to a medium containing at least one pancreatic islet differentiation-inducing compound to provide an environment that promotes proliferation of differentiated pancreatic cell types. Pancreatic morphology in precursor cells becomes evident after exposure to the pancreatic islet differentiation-inducing compound and becomes more evident steadily over time. Pancreatic islet marker expression also becomes apparent after treatment, in particular, insulin secretion. Differentiated pancreatic cell types eventually express other pancreatic markers known to those skilled in the art, such as glucagon.

In one aspect of the invention, the pancreatic islet differentiation-inducing compound for inducing differentiation of nestin-positive endodermal/neuronal precursor cells to insulin-secreting pancreatic islet cells is a growth factor. In a preferred embodiment, the growth factor is basic fibroblast growth factor (bFGF). The invention contemplates other growth factors including but not limited to insulin-like growth factor, epidermal growth factor and nicontineamide.

Progressive differentiation of the nestin-positive, partially differentiated endodermal/neuronal precursor cells to insulin-secreting pancreatic islet cells corresponds with a decrease in nestin expression and an increase insulin production, indicating that differentiated insulin-secreting pancreatic islet cells are produced. Further characterization can be accomplished using known immunocytochemical and antibody techniques. For example, immunocytochemical analysis of insulin-secreting pancreatic islet cells generated in vitro reveals that the cells also express other proteins that are associated with naturally-differentiated pancreatic islet cells.

The invention also includes a method for producing an isolated pancreatic islet cell from isolated marrow stromal cells. The method comprises differentiating an isolated marrow stromal cell in the same general manner as recited above, thereby producing an isolated insulin-secreting pancreatic islet cell.

The differentiated insulin producing pancreatic cells generated as described herein may be further tested to determine their viability in vivo. The insulin producing islet cells may be transplanted, using sterile technique and known and accepted procedures, into individual experimental animals, typically implanted beneath the kidney capsule as disclosed in U.S. Pat. No. 6,001,647.

The invention further includes a method of treating a human patient having a disease, disorder, or condition of the pancreatic endocrine system by administering the differentiated insulin-secreting pancreatic islet cells of the invention to the body of the patient.

The methods disclosed herein encompass introduction of differentiated insulin-secreting pancreatic islet cells and/or other endodermal cells in cell-based therapeutics where a patient is in need of the administration of such cells. The differentiated cells are preferably administered to a human. When isolated insulin-secreting pancreatic islet cells are administered to a patient with diabetes, the insulin-secreting pancreatic islet cells will beneficially influence cells which are already present in the pancreatic system. For example, insulin-secreting pancreatic islet cells which are introduced into the body of the patient may be used to replace non-functioning and/or damaged pancreatic islet cells.

Thus, the methods disclosed herein induce marrow stromal cell differentiation into endodermal cells, particularly insulin-secreting pancreatic islet cells. Such methods are crucial in the development of cell-based therapeutics for treatment of diabetes. Indeed, prior to the present invention, the lack of sources of pancreatic cells that can be introduced into the pancreas of a human patient, has severely impeded the development of Type I and Type II diabetes therapeutics. The adult marrow stem cells constitute a unique and novel source for the production of pancreatic cells for the treatment of diabetes.

The cells produced by the methods disclosed herein are useful in the treatment of Type I diabetes which afflicts two million patients due to pancreatic islet cell damage and requiring insulin injection. It is estimated that thirty-five million patients with Type II diabetes associated with non-responsiveness of target tissues to insulin are treated by insulin injection, a significant portion of which may be replaced through the use of the generated pancreatic islet cells.

The ability to grow functioning islet cells in vitro from the bone marrow stromal cells of an individual represents a major technical breakthrough and facilitates the use of new strategies for treating and studying insulin-dependent diabetes. For example, in accordance with the subject invention, new cultured islets from diabetic individuals can be implanted in a patient as a way to control or eliminate the patient's need for insulin therapy because the cultured islets and/or islet cells are able to produce insulin in vivo.

Induction of Other Endodermal Phenotypes

Additional methods employ cultures optimized to induce differentiation of the nestin-positive endodermal/neuronal precursor cells of the invention into other cells of endodermal lineage including but not limited to gut epithelium and liver cells.

By employing various combinations of factors at different stages, different seeding densities and at different times, MSC cultures may be optimized to preferentially induce differentiation to various desired cell fates. In addition, factors produced by the MSC cultures in the course of differentiation which augment growth of a particular cell type can be isolated, sequenced, cloned, produced in mass quantities, and added to MSC cultures to facilitate growth and targeted differentiation of those cultures. The relevant factors are identified by concentrating MSC culture supernates from early, intermediate and late stages of differentiation and testing for the ability of these concentrates to augment MSC growth and differentiation into the target population. Positive effects for the desired cell type are correlated with molecular constituents in the concentrates by two-dimensional gel electrophoresis of positive and negative supernates, purification and N-terminal sequencing of spots present only in the positive concentrates and subsequent cloning and expression of the genes encoding these factors.

The invention further includes a method of treating a human patient having a disease, disorder, or condition associated with tissues of endodermal origin by administering particular differentiated endodermal cells of the invention to the body of the patient. The methods disclosed herein encompass introduction of differentiated endodermal cells in cell-based therapeutics where a patient is in need of the administration of such cells. The differentiated cells are preferably administered to a human. The precise site of administration of the differentiated cells will depend on any number of factors, including but not limited to, the site of a lesion to be treated, the type of disease being treated, the age of the human and the severity of the disease, and the like. Determination of the site of administration is well within the skill of the arstisan versed in the administration of cells to animals.

As a result, these MSC derived precursor cells create a potential therapeutic treatment for a variety of other diseases associated with of endodermal origin, including but not limited inflammatory bowel disease, stomach cancer, colon cancer, colo-rectal cancer and liver disease. Determination of the site of administration is well within the skill of the artisan versed in the administration of cells to mammals. Cells may be introduced by direct injection, by using a shunt, or by any other means used in the art for the introduction of compounds into any of several organ systems.

Tissue Engineering

The subject invention also greatly facilitates genetic engineering of endodermal cells, particularly islet cells, to resist subsequent immunological destruction. For example, cultured islet cells can be transformed to express a protein or peptide which will inhibit or prevent the destructive immune process. Other useful proteins or peptides may be expressed. In addition, expression of specific autoantigens, such as GAD, 64 kD islet cell surface antigens (see Payton et al., 1995), or any other markers identified on the differentiated pancreatic cells, can be eliminated by standard gene knockout or selection procedures to produce differentiated pancreatic cells which are not susceptible or are less susceptible to auto-immune attack. Methods for producing such mutant or knock out cell lines are well known in the art and include, for example, homologous recombination methods disclosed in U.S. Pat. Nos. 5,286,632; 5,320,962; 5,342,761; and in WO 90/11354; WO 92/03917; WO 93/04169; WO 95/17911, all of which are herein incorporated by reference for this purpose.

Moreover, the subject invention contemplates the in vivo use of in vitro grown MSCs to produce pancreas-like structures or an "ecto-pancreas" organ that exhibits functional, morphological and histological characteristics similar to those observed in a normal pancreas. Thus, the ability to produce a functional "ecto-pancreas" in vivo from in vitro grown pancreatic cells can be used to treat, reverse or cure a wide variety of pancreatic diseases.

Definitions

The articles "a" and "an" are used herein to refer to one or to more than one (i.e. to at least one) of the grammatical object of the article. By way of example, "an element" means one element or more than one element.

As used herein, "stromal cells", "isolated marrow stromal cells" and "MSCs" are used interchangeably and are meant to refer to the small fraction of cells in bone marrow which can serve as stem cell-like precursors of osteocytes, chondrocytes, adipocytes and various other cell types and which are isolated from bone marrow by their ability adhere to plastic dishes. Marrow stromal cells may be derived from any animal. In some embodiments, stromal cells are derived from primates, preferably humans.

As used herein, the term "isolated" referring to a cell is meant to refer to a cell which has been separated from its natural environment. This term includes gross physical separation from its natural environment, e.g., removal from the donor animal, e.g., a rat or human. When used to refer to a population of cells, the term "isolated" includes populations of cells which result from proliferation of the isolated cells of the invention. For uses requiring a pure population of the endodermal cells produced by the present invention, particularly insulin-secreting pancreatic islet cells, the differentiated cells of the invention can be isolated from a mixture of cells by several methods known in the art.

As used herein, the term "anti-oxidant" is meant to refer to those substances that inhibit oxidation or reactions promoted by oxygen or peroxides. Examples of anti-oxidants include, but are not limited to, beta-mercaptoethanol, dimethylsulfoxide, butylated hydroxytoluene, butylated hydroxyanisole, ascorbic acid, dimethylfumarate, and n-acetylcysteine.

As used herein, the terms "beneficial protein or peptide" and "therapeutic protein or peptide" are used interchangeably and are meant to refer to a protein or peptide, for example insulin, which can compensate for the protein encoded by a defective gene and/or insufficient gene expression that is causally linked to the disease or symptoms of the disease, disorder or condition characterized by a gene defect. The presence of the protein alleviates, reduces, prevents or causes to be alleviated, reduced or prevented, the causes and/or symptoms that characterize the disease, disorder or condition.

As used herein, a disease, disorder or condition which can be treated with a beneficial or therapeutic protein or peptide is meant to refer to a disease, disorder or condition that can be treated or prevented by the presence of a protein which alleviates, reduces, prevents or causes to be alleviated, reduced or prevented, the causes and/or symptoms that characterize the disease, disorder or condition. Diseases, disorders and conditions which can be treated with a beneficial protein or peptide include diseases, disorders and conditions characterized by a gene defect as well as those which are not characterized by a gene defect but which nonetheless can be treated or prevented by the presence of a protein which alleviates, reduces, prevents or causes to be alleviated, reduced or prevented, the causes and/or symptoms that characterize the disease, disorder or condition.

The term "isolated nucleic acid" should be construed to refer to a nucleic acid sequence, or segment, or fragment which has been purified from the sequences which flank it in a naturally occurring state, e.g., a DNA fragment which has been removed from the sequences which are normally adjacent to the fragment e.g., the sequences adjacent to the fragment in a genome in which it naturally occurs. The term also applies to nucleic acids which have been substantially purified from other components which naturally accompany the nucleic acid, e.g., RNA or DNA or proteins which naturally accompany it in the cell.

As used herein, "transfected cells" is meant to refer to cells to which a gene construct has been provided using any technology used to introduce nucleic acid molecules into cells such as, but not limited to, classical transfection (calcium phosphate or DEAE dextran mediated transfection), electroporation, microinjection, liposome-mediated transfer, chemical-mediated transfer, ligand mediated transfer or recombinant viral vector transfer.

The term "differentiation" as used herein, should be construed to mean the induction of a differentiated phenotype in an undifferentiated cell by coculturing the undifferentiated cell in the presence of a substantially homogeneous population of differentiated cells, in the presence of products of differentiated cells or in the presence of an inducer of cell differentiation.

The term "endodermal cell" as used herein should be construed to mean a cell expressing a phenotype characteristic of a cell normally associated with a tissue derived from the endodermal embryonic germ layer.

The term "endodermal/neuronal precursor cell" as used herein should be construed to mean an MSC partially differentiated such that it expresses nestin and has the potential to further differentiate into an endodermal and/or a neuronal cell phenotype.

The term "endodermal/neuronal precursor-inducing compound" as used herein is meant to refer to those compounds capable of inducing differentiation of a stromal cell into a nestin-positive endodermal/neuronal precursor cell.

The term "insulin-secreting pancreatic islet cell" as used herein should be construed to mean an MSC differentiated such that it expresses the pancreatic islet marker insulin.

The term "neuron" as used herein should be construed to mean a nerve cell capable of receiving and conducting electrical impulses from the central nervous system. A nerve cell or "neuron" typically comprises a cell body, an axon, axon terminals, and dendrites and is derived from the ectodermal embryonic germ layer.

The term "endodermal differentiation-inducing compound" is meant to refer to those compounds capable of inducing differentiation of a nestin-positive endodermal/neuronal precursor cell into an endodermal cell. These compounds include, but are not limited to antioxidants, trophic factors, and growth factors.

The term "pancreatic islet differentiation-inducing compound" is meant to refer to those compounds capable of inducing differentiation of a nestin-positive endodermal/neuronal precursor cell into a pancreatic islet cell. These compounds include, but are not limited to antioxidants, trophic factors, and growth factors.

The invention is further described in detail by reference to--the following specific examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLES

In a particular embodiment set forth as follows, adult rat stromal cells are expanded as undifferentiated cells in culture for a sufficient number of passages to indicate their proliferative capacity. This exemplary treatment protocol induces the stromal cells to exhibit a pancreatic phenotype including pancreatic islet cell morphology and expression of various pancreatic-specific markers.

Human marrow stromal cells treated using the novel protocol exemplified herein differentiate into pancreatic cells similarly to rat MSCs. Thus, the protocol is not limited to rodent stromal cells. By use of the strategies exemplified herein, mammalian marrow stromal cells can be induced to differentiate into insulin-secreting pancreatic islet cells.

Cultures

Rat MSCs are originally cultured in alpha-Modified Eagle's Medium (alpha-MEM) supplemented with 20% FBS, 2 mM L-glutamine, 100 units per milliliter penicillin, 100 milligrams per milliliter streptomycin and 25 nanograms per milliliter amphotericin B. For each passage the cells are plated at about 8,000 cells per square centimeter and grown to confluency. At passage 6 the cells are transferred to DMEM (pH 8.0)/20% FBS without additional supplementation, and maintained beyond passage 14. Sub-confluent cultures of rat and human MSCs are maintained in DMEM/20% FBS.

Twenty-four hours before induction of partial differentiation to nestin-positive precursor cells, medium is replaced with a pre-induction medium consisting of DMEM, 20% FBS and 1 millimolar $\beta$-mercaptoethanol. The cells are then transferred to a serum free endodermal/neuronal precursor induction medium composed of DMEM and 1-10 millimolar $\beta$-mercaptoethanol. Under these circumstances, the cells begin to express nestin indicating that they are partially differentiated, potentially endodermal and/or neural precursors. To effect further differentiation to pancreatic islet cell phenotype, the partially differentiated nestin-positive endodermal/neuronal precursor cells are transferred to serum-free DMEM containing 1-10 mM $\beta$-mercaptoethanol with and without 10 nanograms/ml basic fibroblast growth factor (bFGF).

In parallel preparations, the precursor induction medium is composed of DMEM and 200 micromolar butylated hydroxyanisole and the nestin-positive endodermal/neuronal precursor cells are transferred to serum-free DMEM containing 1-10 mM butylated hydroxyanisole with and without 10 nanograms/ml bFGF.

Pancreatic/Neuronal Precursor Characterization rMSCs are initially maintained in sub-confluent cultures in pre-induction media supplemented with 1 mM beta-mercaptoethanol (BME) for 24 hours. Under these conditions no changes in morphology are evident. To effect differentiation into pancreatic/neuronal precursor cells, the cells are transferred to serum-free medium containing 1-10 millimolar BME (SFM/BME). Within 5 hours of exposure to SFM/BME the cells begin to express nestin.

Insulin-Secreting Pancreatic Islet Cell Characterization

Nestin-positive endodermal/neuronal precursor cells from the precursor induction medium are transferred to serum free medium containing 1-10 mM mercaptoethanol with bFGF (SFM/BME/bFGF) and without bFGF (SFM/BME). The expression of nestin decreases over time as the cells mature and eventually differentiate to insulin-secreting pancreatic islet cells. This is associated with a concomitant increase in insulin secretion by the differentiated cells.

To examine the effects of different anti-oxidants in mediating the induction of differentiation in MSCs to endodermal/neuronal progenitors, rMSCs may be treated with other anti-oxidants, e.g., dimethylsulfoxide (DMSO), butylated hydroxyanisole (BHA), or butylated hydroxytoluene (BHT), ascorbic acid, dimethylfumarate, n-acetyleysteine, and the like, both alone and in combination with each other.

Clonal Analysis

To determine whether individual rMSCs exhibit stem cell characteristics of self-renewal and pluripotentiality, individual clones are analyzed. To establish clones, rMSCs are plated at approximately cells per square centimeters, grown to 50-150 cells per colony, isolated with cloning cylinders, transferred to separate wells and eventually to individual flasks. Stem cell characteristics are confirmed when single cells replicate as typical rMSCs and differentiate into insulin secreting pancreatic islets cells after treatment.

Human Stromal Cells Differentiate into Insulin Secreting Pancreatic Islet Cells

The pancreatic and/or neuronal cell potential of MSCs is not unique to rodents as can can be demonstrated by previous experiments using MSCs obtained from humans (hMSCs). In those studies, hMSCs were isolated from a healthy adult donor and grown in vitro (Bjornson et al., 1999, Science 283:534-537). hMSCs resembled their rodent counterparts, growing as large flat cells in the undifferentiated state. Human marrow stromal cells subjected to the pancreatic differentiation protocols disclosed will attain pancreatic islet cell characteristics in a time frame similar to that observed for rMSCs.

Western Blot

Thirty milligrams of protein extract from untreated (U), BME induced (I), and BME/bFGF-induced (II) rMSC pancreatic cultures are separated on a 4%-20% gradient acrylamide gel and electrophoretically transferred to a nylon membrane. The Western blot is probed for insulin expression using an anti-insulin monoclonal antibody followed by secondary antibody conjugated with horse radish peroxidase (HRP). Color development is performed using enhanced chemiluminescence reagents.

The blot is then stripped and probed for nestin expression using anti-nestin polyclonal antibody. Again, the secondary antibodies are BRP-conjugated, and color is developed using ECL reagents.

Immunocytochemistry

Cultured rMSCs are fixed with 4% paraformaldehyde, incubated with primary antibody overnight at 4° C., incubated with secondary antibody for one hour, followed by exposure to avidin-biotin complex for one hour at 25° C. Diaminobenzidene (DAB) serves as chromogenic substrate for HRP.

FM1-43 Labeling

Cultures are treated with DMSO/BHA in serum-free media (SFM) for approximately 4 hours. The cells are maintained for an additional 30 minutes in artificial cerebral spinal fluid (aCSF)/BHA. Cells are labeled in aCSF containing I millimolar FM1-43 and 75 mM KCI for 60 seconds. The labeling mixture is removed, the cultures are washed twice with aCSF, and the cells are incubated in aCSF for 60 minutes to reduce background staining. Cultures are fixed with 4% paraformaldehyde, and soaked for 24 hours in phosphate buffered saline (PBS) before analysis.

Stromal Cell Characterization

Rat mesenchymal stromal cells (rMSCs) are isolated from the femurs of adult rats and propagated in vitro (Azizi et al., 1998, Proc. Natl. Acad. Sci. USA 95:3908-3913). The data disclosed from previous experiments shown in FIG. 9A demonstrate that the distribution of cells stained with antibody to CD19B (unfilled) does not differ from that of isotype control (filled), indicating the rMSC cultures do not contain significant numbers of contaminating CD 11b-expressing cells. The absence of hematopoietic precursors in the stromal cell cultures prepared according to the method of the invention may also be verified. FIG. 9B also demonstrates that in previous studies, the intensity of staining does not differ between CD45 antibody (unfilled) and control (filled) profiles, indicating that rMSCs cultured according to the present invention methods are not contaminated by CD45-expressing cells. Fluorescent cell sorting at passage 1 also demonstrates that the cells are negative for CD11b (FIG. 9A), and CD45 (FIG. 9B), which are cell surface markers associated with lymphohematopoietic cells.

Rat MSCs also express CD90 (FIG. 9C), consistent with their undifferentiated state.

At the outset of the pancreatic differentiation disclosed elsewhere herein, untreated rMSCs are further characterized by staining for the cell surface markers CD44 and CD71. Cells positive for CD44 and CD71 expression, are consistent with previous reports (Pittenger et al., 1999, Science 284:143-147; Bruder et al., 1998, Clin. Orthop. Relat. Res. 355S:S247-S256).

To the best of Applicants' knowledge, this is the first report that peripheral mesenchymal cells can differentiate into cells of endodermal lineage in vitro. In particular, the present invention provides methods of directing differentiation of MSCs into insulin producing pancreatic islet cells in vitro. MSCs are useful in the treatment of a wide variety of diseases disorders and conditions, and these cells offer significant advantages over other so-called "stem" cells. That is, bone marrow cells are readily accessible and provides a renewable population which can be expanded in vitro thereby allowing complex gene manipulations to be performed for ex vivo gene therapy and/or for cell therapy for endodermal diseases, disorders or conditions that require administering cells to the site of an endodermal organ. Furthermore, autologous transplantation overcomes the ethical and immunologic concerns associated with the use of fetal tissue. Moreover, MSCs grow rapidly in culture, precluding the need for immortalization, and are capable of differentiating into cells normally derived from multiple lineages including insulin producing pancreatic islet cells produced according to the protocols disclosed herein.

The following observations suggest that untreated MSCs are "multidifferentiated" and that further differentiation to specific phenotypes, for example neuronal or pancreatic phenotypes, comprises quantitative modulation of gene expression rather than simple on-off switching of phenotypically specific genes.

MSCs normally differentiate into bone, cartilage, muscle, tendon and fat, classical mesenchymal derivatives (Owen, 1988; Beresford, 1989; Young et al., 1998; Pittenger et al., 1999). We recently found that MSCs can be induced to overcome their mesenchymal fate and differentiate into neurons in vitro (Woodbury et al., 2000). Treatment with a relatively simple, fully defined medium elicited neuronal differentiation of approximately 80% of the cells. Within five hours, the MSCs formed characteristic refractile spherical cell bodies, extended typical long neuritic processes exhibiting terminal expansions and filopodia. The treated MSCs expressed the neuroepithelial gene product, nestin, transiently, the neuronal products neurofilament M (NF-M), tau and Neu-N de novo, and increased expression of neuron-specific enolase (NSE). These unanticipated observations indicate that MSCs may be useful in the treatment of a number of neurological diseases, and raise basic questions regarding stem cell biology and mechanisms of differentiation. In addition, the discovery that developing islet cells also express nestin (H. Zulewski et al., 2001, Diabetes 50: 521) points to the potential of MSCs as sources of insulin producing pancreatic islet cells.

MSCs Express Diverse Genes

To begin characterizing the undifferentiated MSCs more fully, we examined expression of a representative spectrum of genes that included those specific for diverse lineages. Our initial microarray screen of cultured dissociates revealed that the MSCs expressed many genes associated with differentiated cells. The expressed genes were not limited to mesodermal lineages, but included genes representative of all germ layers.

Figure 1:
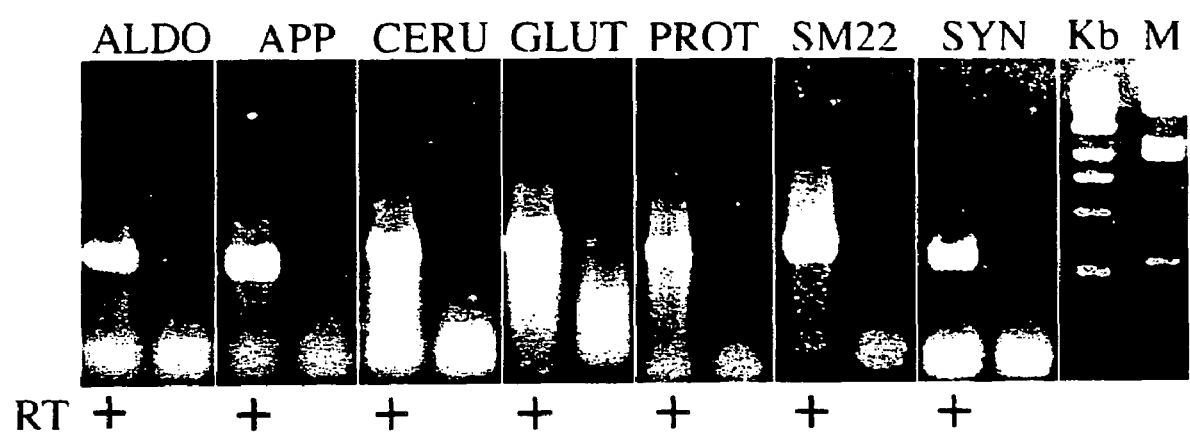
FIG. 1. Undifferentiated MSCs express genes representative of all germ layers. Messenger RNA was harvested from undifferentiated MSCs, converted to cDNA, and target genes were amplified using specific primer pairs (see Table 1 for symbol and primer sequences). Amplification resulted in a single band in each reaction where cDNA target was provided (RT+). Control lanes, where no RTase was present during the cDNA synthesis reaction, did not yield product. Kilobase ladder (Kb) and λ/Hind III DNA (M) were employed as markers.
Figure 2:
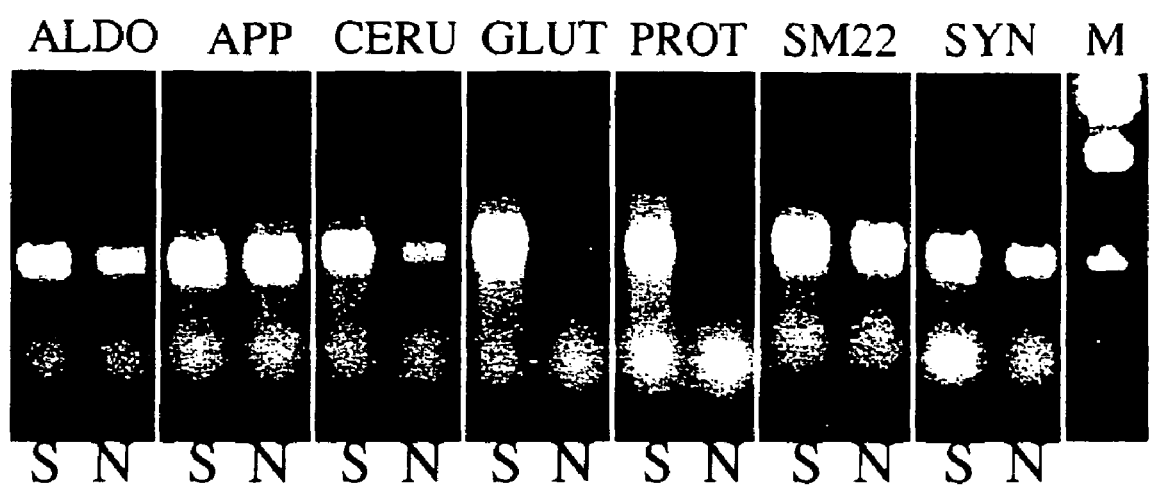
FIG. 2. Neuronal differentiation of MSCs alters the pattern of gene expression. RNA was harvested from undifferentiated MSCs (S) or from MSC-derived neurons (N) 48 hours after neuronal induction. RT-PCR was performed to amplify gene products representing specific germ layers.

To confirm this unexpected observation, we assayed transcript levels by RT-PCR, focusing on prototypical genes specific for different germ layers. In addition to expression of expected mesodermal messages, such as SM22α, RT-PCR revealed mRNA for endodermal ceruloplasmin, ectodermal syntaxin, aldolase C, glutamate receptor binding protein and APP (amyloid precursor protein), and germline protamine2 (FIG. 1; Table 1). Omission of RTase in controls eliminated PCR products, confirming that the signals observed in the experimental groups were derived from RNA transcripts and not contaminating genomic DNA (FIG. 1).

Expression of additional mRNA species identified by microarray, including mesodermal myosin and leptin, and neural N-methyl-D-aspartate receptor subunit 1 (NMDA R1) was also confirmed by RT-PCR.

Gene Expression During Neuronal Differentiation

While the expression of diverse gene products characteristic of distinct lineages by "undifferentiated" MSCs was unexpected, it may reflect extensive plasticity intrinsic to this stem cell population. Differentiation to specialized cell types, in turn, might be expected to differentially alter transcription of subsets of these messages. To examine this contention, we subjected MSCs to the neuronal differentiation protocol, harvested RNA after 48 hours, and assessed expression of the foregoing prototypical target genes by RT-PCR. In fact, neuronal differentiation significantly altered the pattern of gene expression. Induction decreased the transcription of germline protamine2 to undetectable levels. Similarly, endodermal ceruloplasmin dramatically decreased. Perhaps unexpectedly, NMDA receptor binding protein also decreased. Expression of the neural genes aldolase C and syntaxin exhibited modest decreases, as did muscle-specific SM22α. Among the genes surveyed, only APP expression remained unchanged as the MSCs assumed neuronal morphologic characteristics, allowing this signal to serve as an internal control, confirming that equal amounts of cDNA were present in each reaction.

We had previously found that the neuron-specific intermediate filament, NF-M is expressed by MSC-derived neurons, but not by undifferentiated MSCs (Woodbury et al., 2000). Here, we employed NF-M expression as a temporal, quantitative index of neuronal differentiation to help place the present observations in context. NF-M expression is associated with initiation of neuritogenesis, neural process outgrowth and assumption of the characteristic mature neuronal morphology (Carden et al., 1987).

MSCs maintained in serum free medium for 24 hours exhibited extremely low, but detectable levels of NF-M mRNA by RT-PCR, consistent with adoption of neuronal morphologies by a small number of cells under these conditions. However, incubation with the neural induction medium for 24 hours greatly enhanced NF-M message levels, consistent with differentiation of the vast majority of MSCs into neurons (FIG. 3A). As a positive control, we detected NF-M in the cerebellum of 32-day-old rats, generating a single band of the expected size (FIG. 3A). The encephalizing gene noggin (Smith and Harland, 1992) was unchanged 24 hours after neural differentiation, establishing the specificity of the increase in NF-M (FIG. 3). To define the temporal profile of differentiation, we examined NF-M transcript levels 5 and 24 hours after initiation of induction. NF-M was undetectable after 5 hours of incubation in serum free medium, and was just above the level of detection after 5 hours in neuronal induction medium (FIG. 3B). Transcript abundance increased dramatically at 24 hours, consistent with previous observations. In aggregate, our observations indicate that assumption of neuronal morphologies by MSCs is accompanied by a dramatic increase in the prototypical neuronal gene, NF-M, complex modulation of other neuronal genes, and decreased transcription of germline and mesodermal genes.

Expression of Neuroglial Genes

Figure 4A:
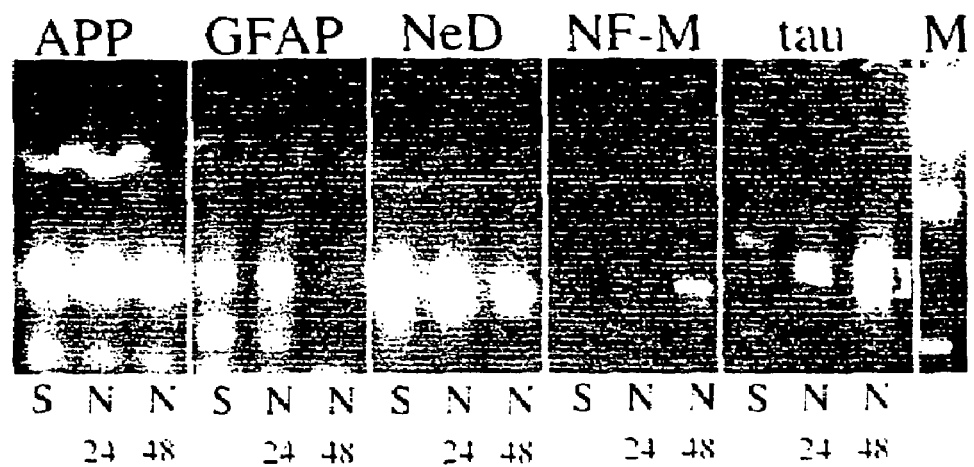

Having established the utility of RT-PCR in defining the unexpected expression of diverse differentiated genes in the "undifferentiated" MSCs and in neuronal differentiation, we examined transcriptional regulation of genes specific to the neuroglial lineage. APP served as a control, ensuring that equal amounts of target cDNA were used in each reaction (FIG. 4). We examined GFAP (glial fibrillary acidic protein), the classical astrocyte marker (Eng et al., 197 1), which is also expressed in neuroglial precursor cells (Laywell et al.; 2000; Doetsch et al., 1999). Uncommitted MSCs expressed GFAP (FIG. 4A). With neuronal differentiation, the gene product was detectable at 24 hours, but 48 hours post-neuronal induction was no longer discernible, consistent with neuronal, but not glial differentiation. Nevertheless, expression of GFAP by the MSCs is consistent with a growing body of evidence indicating that neural precursors in vivo express neuronal and glial markers and can differentiate into either lineage.

To begin assessing mechanisms regulating neuronal differentiation, we examined NeuroD, a transcription factor transiently expressed in neuronal precursor cells, known to regulate neuronal fate decisions (Lee, 1997; Morrow et al., 1999). Robust expression of NeuroD was detected in the uncommitted MSCs, suggesting that these undifferentiated cells were already "primed" for neural differentiation (FIG. 4A). With differentiation, NeuroD progressively decreased, and was markedly diminished by 48 hours, consistent with transient expression of the transcription factor in differentiating neurons (Lee et al., 1995).

Figure 4B:
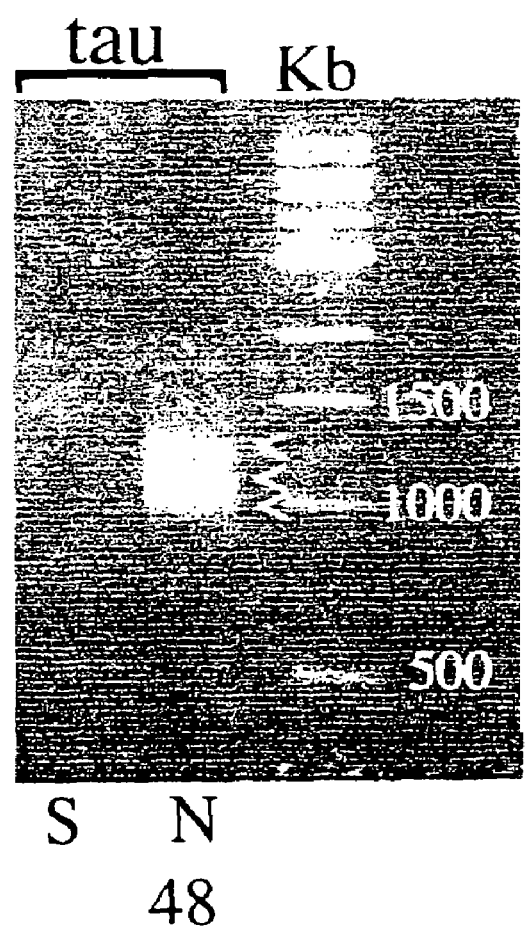

We used NF-M and tau as neuron-specific marker prototypes to examine translation with neuronal differentiation. Consistent with our previous findings, NF-M mRNA was undetectable in uncommitted MSCs, but was present after 48 hours of neuronal induction. Tau transcripts were not detectable in the uncommitted MSCs, but were present in MSC-derived neurons (bracketed bands) consonant with early stages of neuronal differentiation. This finding is consistent with our previous studies indicating that tau is not expressed by MSCs but is present in MSC-derived neurons (Woodbury et al., 2000). Analysis of the tau transcripts revealed that the known tau mRNA isoforms, generated by alternative splicing of exons 2 and 3 (Goedert et al., 199 1), were present in the MSC-derived neurons (FIG. 4B). Collectively, these data indicate that incubation in NIM decreases the expression of neural precursor messages (GFAP, NeuroD), while simultaneously increasing the expression of specific neuronal markers (NF-M, tau), consistent with ongoing neuronal differentiation.

Figure 5A:
Figure 5B:
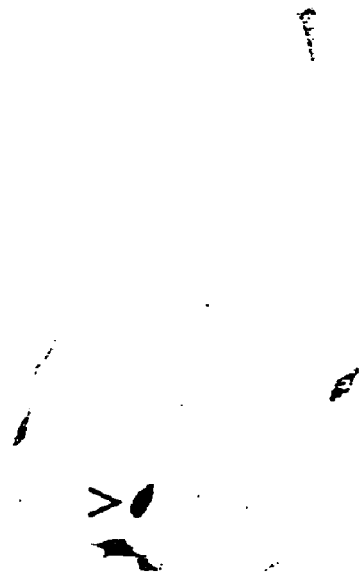

Expression of tau was confirmed at the protein level immunocytochemically. MSC-derived neurons, maintained in NIM for 10 days were probed with anti-tau antibody. There was significant heterogeneity in the level of tau expression in the neurons even after 10 days, which often correlated with the degree of neuronal morphologic differentiation. For example, abundant intensely tau-positive neurons (>) with long varicose (arrows) processes were evident, whereas neighboring cells exhibiting immature, transitional morphologic features displayed weak staining (FIG. 5A). Heterogeneity of staining is further exemplified in FIG. 5B. Cells in the field exhibit neuronal morphological characteristics and definitive tau positivity, yet staining intensity varies from cell to cell. Many cells in this culture (>) have elaborated long processes which terminate in growth cone-like structures (arrow).

Figure 6A:
Figure 6B:
Figure 6C:
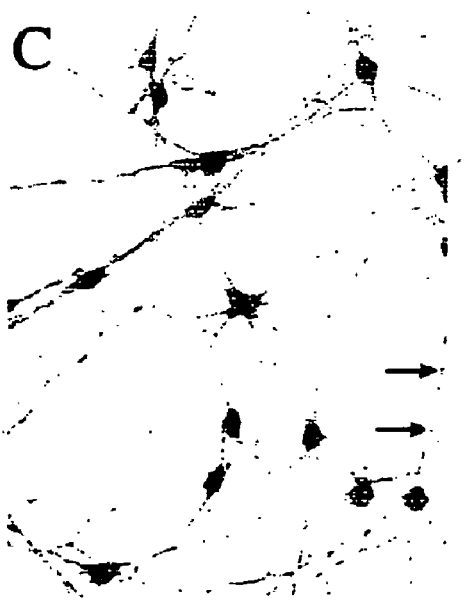

We examined additional neuronal gene products that are expressed in more mature neurons or that are associated with functional neuronal communication. At 10 days, the MSC-derived neurons uniformly expressed TOAD-64, a neuron-specific protein thought to play a role in axonal pathfinding (Minturn et al., 1995) (FIG. 6A). Similarly, β-tubulin 111, an intermediate filament characteristic of mature neurons (Menezes and Luskin, 1994) was present in virtually all cells (FIG. 6B). In contrast to these neuronal markers, O-4, a classic oligodendrocyte gene product, and MBP, a marker for mature oligodendrocytes, were not detectable in MSC-derived neurons (data not shown).

Genes Associated with Neurotransmission

Figure 6D:
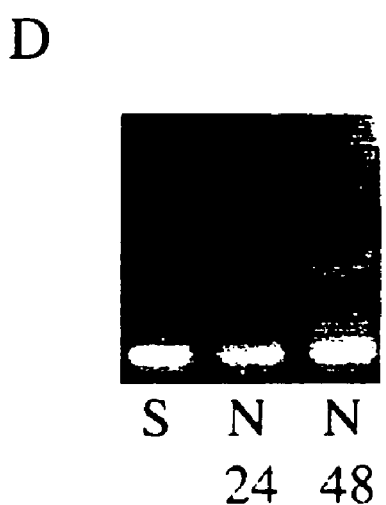

To begin assessing the developing ability for functional communication, we initially examined synaptophysin, which is associated with synaptic vesicles and transmission. The protein was detected in cell bodies as well as varicose, putative transmitter release sites along processes, reflecting an immature pattern of distribution (FIG. 6). Analysis by RT-PCR indicated that synaptophysin m. RNA was not present in undifferentiated MSCs, but was detectable after 24 hours of neuronal differentiation, and continued to increase thereafter (48 hrs.) (FIG. 6D).

Figure 7A:
Figure 7B:
Figure 7C:
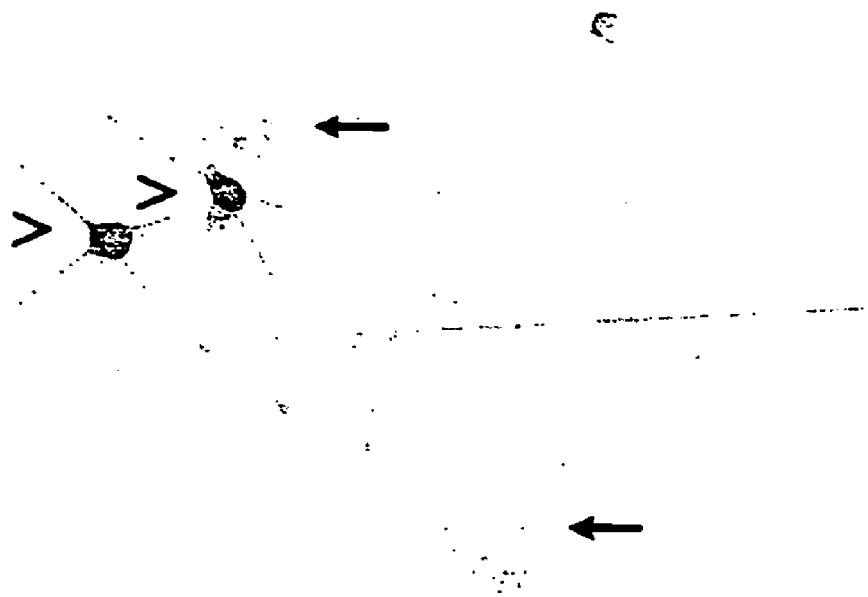
Figure 7D:

To further assess the developing capability for communicative function, we examined the expression of neurotransmitter enzymes. At 10 days, a large population of the neurons expressed choline acetyltransferase (ChAT), which catalyzes the synthesis of the excitatory transmitter, acetylcholine (FIG. 7A, 7B). A similar percentage of ChAT-positive cells was seen when a monoclonal ChAT antibody from a different commercial source was used for staining, validating this staining pattern (data not shown). Interestingly, the majority of neurons (>85%) derived from the multipotent P19 embryonal carcinoma cell line are also cholinergic (Parnas and Linial, 1995). A smaller subpopulation of MSC-derived neurons expressed tyrosine hydroxylase, the rate-limiting enzyme in the synthesis of catecholamines, dopamine, norepinephrine and epinephrine (FIG. 7C, 7D). In aggregate, these observations indicate that the MSC-derived neurons were developing the structural apparatus for synaptic communication and the machinery for transmitter signal biosynthesis. The expression of enzymes for different transmitters suggests that the MSC-derived neurons are capable of differentiating into multiple subtypes.

Morphologic Reversion and Gene Expression

Figure 8A:
Figure 8B:
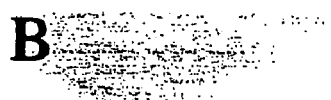
Figure 8C:
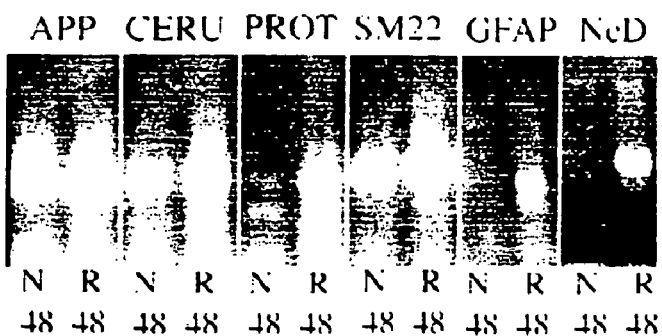

Neuronal differentiation of MSCs exhibited notable plasticity at its earliest stages, when it was partially reversible. Cells exposed to NIM assumed characteristic neuronal morphologies, displaying refractile cell bodies and long processes by 24 hours post-induction (FIG. 8A). Withdrawal of NIM from MSC-derived neurons elicited process retraction and reversion of morphology within 24 hours to flat cells, which shared characteristics with uncommitted MSCs but generally displayed a more stellate morphology (FIG. 8B). To assess changes in gene expression associated with reversion, MSCs were differentiated to neurons by exposure to NIM for 24 hours. At this time, NIM was removed from half of the cells and replaced with SFM, while the remaining cells were maintained in NIM. Twenty-four hours later (48 hours in total) we harvested RNA from neuronal and reverted cells and assessed changes in gene expression by RT-PCR. We again assayed expression of the archetypal targets from various germ layers expressed at high levels in uncommitted MSCs. Reversion from the neuronal to MSC phenotype was associated with striking changes in expression of a subset of the target genes. Germline protamine2 mRNA, which decreased dramatically with neuronal conversion, increased markedly in the reverted MSCs. Similarly, endodermal ceruloplasmin message increased in MSCs from depressed levels in the neurons. Strikingly, NeuroD mRNA reappeared in the MSCs, presumably indicating the potential for re-differentiation into neurons. GFAP message was also re-expressed, consistent with, reversion to a primitive neuroglial precursor state. In sum, the reverted MSCs appear to re-express multipotentiality, consistent with plasticity at the time of differentiation. In contrast, expression of several genes was unchanged by reversion to MSCs; message levels for APP, muscle specific SM22α (FIG. 8C), syntaxin, and aldolase C (data not shown) remained the same.

Multidifferentiation of MSCs

Far from being undifferentiated, blank slates, the MSCs actively transcribe genes specific for all the classical embryonic germ layers. As expected, the stromal cells express prototypical mesodermal genes, including SM22a, myosin and leptin. In addition, however, MSCs express protamine2, which is germline-specific (Domenjoud et al., 1991), indicative of an early, uncommitted state. Simultaneously, endodermal ceruloplasmin, expressed at high levels in the fetal and adult liver and lung (Fleming and Gitlin, 1990), is transcribed in uncommitted MSCs. Likewise, ectodermal syntaxin 13, highly enriched in the brain (Advanti et al., 1998), and brain-specific aldolase C (Mukai et al., 1991) are expressed by MSCs. NMDA glutamate binding protein (Kumar et al., 1991) and APP (Shivers et al., 1988) represent additional neural genes transcribed by MSCs. These observations are consistent with our previous finding that the MSCs express low levels of neuron-specific enolase (Woodbury et al., 2000).

It may be concluded that MSCs are not "undifferentiated", but rather "multidifferentiated". Recently Labat and co-workers (2000) have proposed the existence of a monocytoid ectomesenchymal stem/progenitor cell that expresses both neural and mesenchymal gene products. Previous work by Enver and colleagues has demonstrated that lymphohematopoietic marrow stem cells express genes characteristic of multiple hematopoietic lineages prior to unilineage commitment (Hu et al., 1997; Cross and Enver, 1997; Enver and Greaves, 1998). Moreover, MSCs co-express genes specific for a number of mesenchymal lineages, including adipocytes, osteoblasts, fibroblasts, and muscle (Seshi et al., 2000). The present work extends these observations, indicating that MSCs transcribe germline, endodermal and ectodermal genes, in addition to mesodermal genes. Our observations imply, consequently, that genes specific for multiple lineages are accessible for transcription in the MSCs, allowing for diverse differentiative fates. Indeed, bone marrow cells have already been shown to give rise to skeletal muscle, hepatocytes, glia and neurons, in addition to the aforementioned mesenchymal derivatives (see Morrison, 2001 for review, and references therein). One might anticipate that MSCs are capable of generating a far larger spectrum of cell types. In the case of neuronal differentiation, prior multidifferentiation may help elucidate aspects of the process, and begin to approach underlying mechanisms. One striking feature of MSC neuronal differentiation is rapidity: Within 5 hours of exposure to the induction medium, the cells assume typical neuronal morphological features and express a variety of neuron-specific genes (Woodbury et al., 2000; present studies). The prior expression of neuronal genes by the MSCs may explain this rapid response. Presumably, quantitative alteration in genes already being transcribed obviates the need for elaboration of new transcription factors or histone acetylation, for example.

Expression of NeuroD by MSCs

Similarly, the expression of NeuroD by the MSCs may also account for the speed of differentiation, and may provide insight into regulatory mechanisms. NeuroD family members, bHLH transcription factors, are transiently expressed in neuronal precursors, and initiate neuronal differentiation (Lee, 1997). These factors appear to function as master regulators of mammalian neurogenesis, as transfection of murine embryonic carcinoma cells with NeuroD2 transcripts initiates neural differentiation in non-neural cells (Farah et al., 2000). In the neural retina, NeuroD plays a role in multiple developmental functions, including retinal cell fate determination, differentiation and neuron survival (Morrow et al., 1999). In this model system NeuroD induces withdrawal from the cell cycle, regulates neuronal vs. glial cell fate decisions, and favors amacrine vs. bipolar differentiation. The expression of NeuroD by MSCs and its decrease with neuronal differentiation is consistent with a role in stromal conversion to neurons, a contention that we are presently examining experimentally. Moreover, the reappearance of NeuroD in neurons that have reverted to the MSC phenotype is particularly provocative, suggesting that the neuronal potential is an intrinsic property even of stromal stem cells de-differentiated "from neurons."

MSCs as Neuroglial Precursors

Unexpectedly, the undifferentiated MSCs expressed glial as well as neuronal genes. GFAP, the traditional astrocytic marker, is expressed in the MSCs, but decreased with neuronal differentiation. The gene product was detectable 24 hours after neural induction, but by 48 hours was undetectable, consistent with neuronal, but not glial differentiation. Consequently, neuronal differentiation of MSCs exhibits commonalities with neuronal differentiation in the normal adult rodent brain in which neurons derive from neuroglial precursors that express GFAP as well as neuronal characters (Laywell et al., 2000; Doetsch et al., 1999). Although the MSCs expressed the astrocyte marker GFAP, 0-4, a traditional oligodendrocyte gene product, and MBP (myelin basic protein), specific for mature oligodendrocytes, were not present. These observations complement our previous work, demonstrating that the primitive intermediate filament, nestin, characteristic of neuroepithelial precursors, is expressed in MSC-derived neurons at 5 hours, but decreases progressively, and is undetectable 6 days after neuronal differentiation, mimicking normal neuronal differentiation in vivo (Woodbury et al., 2000). We tentatively conclude that neuronal differentiation from MSCs exhibits many sequential features of normal neuronal differentiation in vivo.

Plasticity of MSCs and Neurons

Plasticity is apparently maintained for a period of time after MSCs differentiate into neurons. Removal of the neural inducing medium after initial conversion at 48 hours resulted in the striking reversion of neurons to the MSC phenotype within 24 hours. Neuritic processes rapidly contracted and disappeared, cell bodies lost refractility and flattened, and the cells assumed a typical MSC morphology. With reversion, germline protamine2 was re-expressed after becoming undetectable in the neurons. Endodermal ceruloplasmin increased significantly in the reverted MSCs. Most dramatically, in the present context, NeuroD mRNA reappeared in the reverted MSCs, after having disappeared 48 hours after neuronal differentiation, suggesting that the revertants retained the potential for re-differentiation. The reverted MSCs also re-expressed GFAP mRNA after disappearance in the neurons, suggesting that the MSCs have, indeed, regressed to a primitive neuroglial precursor state. The re-expression of a number of functionally critical MSC genes indicates that the cells revert to the multidifferentiated, multipotential state. Our More generally, these observations indicate that fate determination and differentiation are not necessarily irrevocable and unidirectional, but rather may be multidirectional under appropriate circumstances.

Materials and Methods

Marrow Stromal Cell Isolation and Culture. MSCs were isolated from the femurs of adult rats as previously described (Azizi et al., 1998) and maintained in Dulbecco's Modified Eagles Medium (DMEM, Life Technologies) supplemented with 20% Fetal Bovine Serum (FBS, Atlanta Biologicals).

Neuronal Induction. Neuronal differentiation was performed as described (Woodbury et al., 2000) with modification. Briefly, prior to neuronal induction rMSCs were grown in DMEM, 20% FBS, 10 ng/ml bFGF. The monolayer was rinsed twice with PBS and transferred to Neuronal induction media (NIM) consisting of 100 gM BHA, 10 gM forskolin, 2% DMSO, 5 U/ml heparin, 5 nM K252a, 25 mM KCl, 2 mM valproic acid, 1×N2 supplement (Life Technologies), 10 ng/ml bFGF, 10 ng/ml PDGF in a base of DMEM. After induction cells were maintained at 30° C. without further additions. For reversion studies NIM was removed and replaced with unsupplemented DMEM.

RNA Isolation. RNA was isolated from induced and control rMSCs using Trizol reagent according to manufacturer's recommendations (Life Technologies). The resulting RNA pellet was subjected to a chloroform extraction and two ethanol precipitations. Yield was determined spectrophotometrically.

cDNA Synthesis. Two μg of RNA were reverse-transcribed using Superscript 11 Reverse Transcriptase (Life Technologies) in a 50 μl volume containing 1 μg oligo dT primer, 200 μM dNTPs, and buffers supplied by the manufacturer. The reaction was carried out in a Perkin-Elmer 9600 PCR machine with the following parameters: 25° C., 5 minutes; 37° C., 5 minutes; 42° C., 60 minutes; 48° C. 10 minutes. A 5 minute ramp time was employed between each temperature. In control reactions the Superscript 11 reverse transcriptase was omitted.

Polymerase Chain Reaction. 2 to 5 μl of cDNA target was amplified by PCR using specific primer pairs (listed below and in Table 1). Tfl polymerase (Epicentre) and PCR Optimization Kit (Epicentre) were utilized following manufacturer's recommendations. To ensure equal distribution of target a master mix containing all components except specific primers was generated and then aliquoted to each reaction tube. PCR reactions were performed in a Perkin-Elmer 9600 as follows. Initial 3 minute denaturing step at 92° C., followed by 30-35 cycles of 94° C., 5 seconds; 55-65° C., 10 seconds, 68° C., 30 seconds; 74° C., 30 seconds. All reactions were performed in 20 μgl volume.

```
Neurofilament-M (NF-M) Accession # Z12152
F:    AGGTGGCCTTCCTGCGGAGCAATC        SEQ. ID NO. 1

R:    GCCTCAGGAGACTTCACGGGAGAC        SEQ. ID NO. 2 tau Accession # X79321
F:    GGCTTTGAAGCAGCATGGCTGAAC        SEQ. ID NO. 3
```

```
                              -continued
R:    GGCCTGATCACAAACCCTGCTTGG           SEQ. ID NO. 4

NeuroD Accession # D82945
F:    TGACCAAATCATACAGCGAGAGC            SEQ. ID NO. 5

R:    AGAAGTTGCCATTGATGCTGAGCG           SEQ. ID NO. 6

GFAP Primer sequences were based on those
reported in Condorelli et al. (1999)
F:    GAGACGTATCACCTCTGCAC               SEQ. ID NO. 7

R:    GGAAGCAACGTCTGTGAGGT               SEQ. ID NO. 8
```

TABLE 1

| GENE/ACCESS # | SYMBOL | PRIMERS | | LAYER | SEQUENCE ID |
|---|---|---|---|---|---|
| CERULOPLASMIN L33869 | CERU | F: | CTACAGTTGCTCCAACGTTGCCAGG | ENDODERM | SEQ. ID NO. 9 |
| | | R: | AGTAACCAGCTTCCAGGCGTTTGG | | SEQ. ID NO. 10 |
| SM22a L41154 | SM22 | F: | TCTCCTTCCAGTCCACAAACGACC | MESODERM | SEQ. ID NO. 11 |
| | | R: | CTTCCCTTTCTAACTGATGATCTG, | | SEQ. ID NO. 12 |
| PROTAMINE2 X14674 | PROT | F: | ACTATGGITCGCTACCGAATGAGG | GERMINAL | SEQ. ID NO. 13 |
| | | R: | ATCAACATGGAATGGTGTTGTGGC | | SEQ. ID NO. 14 |
| ALDOLASE C M63656 | ALDO | F: | TTGGACTGAGCTACTGTCTGTTGC | ECTODERM | SEQ. ID NO. 15 |
| | | R: | TTTCAGCACACAGCGCCATTTGGC | | SEQ. ID NO. 16 |
| AMYLOID PRECURSOR PROTEIN X07648 | APP | F: | CTCAGAGAACCCTGTGGATGTCCG | ECTODERM | SEQ. ID NO. 17 |
| | | R: | GCATCTCGCTCCAGGTATTTGTAGG | | SEQ. ID NO. 18 |
| NMDA GLUTAMATE BINDING SUBUNIT S61973 | GLUT | F: | AGTTTCTTGGTCTCTGGGACAGC | ECTODERM | SEQ. ID NO. 19 |
| | | R: | AACTGATGGTCAGGATCGACAGGG | | SEQ. ID NO. 20 |
| SYNTAXIN AF044581 | SYN | F: | CTTCAACAGCATCATCCAGACATC | ECTODERM | SEQ. ID NO. 21 |
| | | R: | CACCTTGGTCGTGGATCATCATAGC | | SEQ. ID NO. 22 |

RT-PCR Targets and Representative Germ Layer. Gene targets amplified by RT-PCR, Genbank accession numbers, and representative germ layer are shown. The sequences used to generate primers were specific for the targeted genes. The symbol used to identify targeted genes in the accompanying figures is displayed.

Immunocytochemistry. Cells were fixed in 4% paraformaldehyde and stored under PBS at 4° C. until stained.

Primary antibodies: polyclonal anti-tau, Sigma [1:1000]; polyclonal. anti-TOAD64, Chemicon [1:5000]; monoclonal anti-β-tubulin III, Chemicon [1:200]; monoclonal anti-synaptophysin, Chemicon [1:200]; polyclonal anti-choline acetyltransferase, Chemicon [1:1000]; monoclonal anti-tyrosine hydroxylase, Chemicon [1:1000]. Biotinylated secondary antibodies and peroxidase ABC kit were obtained from Vector. $CoCl_2$ enhanced DAB was used as the chromagen.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

REFERENCES

Advanti, R. J., Bae, H- R., Bock, J. B., Chao, D. S., Doung Y- C., Prekeris, R., Yoo, J- S., and Scheller, R. H. (1998). Seven novel mammalian SNARE proteins localize to distinct membrane compartments. J. Biol. Chem. 273, 10317-10324.

Armstrong, R. J. E., and Svendsen, C. N. (2000). Neural stem cells: From cell biology to cell replacement. Cell Transpl. 9, 139-152.

Beresford, J. N. (1989). Osteogenic stem cells and the stromal system of bone and marrow. Clin. Ortho. Rel. Res. 240, 270-280.

Bjornson, C. R., Rietz, R. L., Reynolds, B. A., Magli, M. C., and Vescovi, A. L. (1999). Turning brain into blood: a hematopoietic fate adopted by adult neural stem cells in vivo. Science 283, 534-537.

Brazelton, T. R., Rossi, F. M. V., Keshet, G. I., and Blau, H. M. (2000). From marrow to brain: expression of neuronal phenotypes in adult mice. Science 290, 1775-1779.

Caplan, A. I. (1991). Mesenchymal stem cells. J. Ortho. Res. 9, 641-650.

Carden, M. J., Trojanowski, J. Q., Schlaepfter, W. W., and Lee, V. M. (1987). Twostage expression of neurofilament polypeptides during rat neurogenesis with early establishment of adult phosphorylation patterns. Neuroscience 7, 3489-3504.

Chang, C., and Hemmati-Brivanlou, A. (1998). Cell fate determination in embryonic ectoderm. J. Neurobiol. 36, 128-15 1.

Clarke, D. L., Johansson, C. B., Wilbertz, J., Veress, B., Nilsson, E., Karlstrom, H., Lendahl, U. and Friesen, J. (2000). Generalized potential of adult neural stem cells. Science 288, 1660-1663.

Condorelli, D. F., Nicoletti, V. G., Barresi, V., Conticello, S. G., Caruso, A., Tendi, E. A., and Giuffrida Stella, A. M. (1999). Structural features of the rat GFAP gene and identification of a novel alternative transcript. J. Neurosci. Res. 56, 219-228.

Cross, M. A. and Enver, T. (1997). The lineage commitment of haemopoietic progenitor cells. Current Opinion in Genetics and Development 7, 609-613.

Deans, R. J., and Moseley, A. B. (2000). Mesemchymal stem cells, Biology and potential clinical uses. Exp. Hematol. 28, 875-884.

Doetsh, F., Caille, I., Lim, D. A., Garcia-Verdugo, J. M., and Alvarea-Buylla, A. (1999). Subventricular zone astrocytes are neural stem cells in the adult mammalian brain. Cell 97, 703-716.

Domenjoud, L., Kren-ding, H., Burfeind, P., Maier, W. M., and Engel, W. (1991). On the expression of protamine genes in the testes of man and other mammals. Andrologia 23, 333-337.

Eglitis, M. A. and Mezey, E. (1997). Hematopoietic cells differentiate into both microglia and macroglia in the brains of adult mice. Proc. Natl. Acad. Sci. USA 94, 4080-4085.

Eng, L. F., Vanderheagen, J. J., Bignami, A., and Gerstl, B. (1971). An acidic protein isolated from fibrous astrocytes. Brain Res. 28, 351-354.

Enver, T., and Greaves, M. (1998). Loops, lineage, and leukemia. Cell 94, 9-12.

Fleming, R. E., and Gitlin, J. D. (1990). Primary structure of rat ceruloplasmin and analysis of tissue-specific gene expression during development. J. Biol. Chem. 265, 7701-7707.

Friedenstein, A. J. (1976). Precursor cells of mechanocytes. Int. Rev. Cytol. 47, 327-355.

Gage, F., Ray, J., and Fisher, L. (1995). Isolation, characterization, and use of stem cells from the CNS. Annu. Rev. Neurosci. 18, 159-192.

Galli, R., Borello, U., Gritti, A., Minasi, M. G., Bjornson, C., Coletta, M., Mora, M., Cusella De Angelis, M. G., Fiocco, R., Cossu, G., and Vescovi, A. L. (2000). Skeletal myogenic potential of human and mouse neural stem cells. Nature Neurosci. 3, 986-991.

Goedert, M., Crowther, R. A., and Garner, C. C. (1991). Molecular characterization of microtubule-associated proteins tau and MAP2. Trends Neurosci. 14, 193-1991

Hu, M., Krause, D., Greaves, M., Sharkis, S., Dexter, M., Heyworth, C., and Enver, T. (1997). Multilineage gene expression precedes conu-nitment in the hemopoietic system. Genes and Dev. 11, 774-785.

Kadiyala, S., Young, R. G., Theide, M. A., and Bruder, S. P. (1997). Culture expanded canine mesenchymal stem cells possess osteochondrogenic potential in vivo and in vitro. Cell Transplantation 6, 125-134.

Kopen, G. C., Prockop, D. J., and Phinney, D. G. (1999). Marrow stromal cells migrate throughout forebrain and cerebellum, and they differentiate into astrocytes after injection into neonatal mouse brains. Proc. Natl. Acad. Sci. USA 96, 1071110716.

Kumar, K. N., Tilalaratne, N., Johnson, P. S., Allen, A. E., and Michaelis, E. K. (1991). Cloning of cDNA for the glutamate binding subunit of an NMDA receptor complex. Nature 354, 70-73.

Kuznetsov, S. A., Friedenstein, A. J., and Robey, P. G. (1997). Factors required for bone marrow stromal fibroblast colonyformation in vitro. Brit. J. Haern. 97, 561570.

Labat, M. L., Milhaud, G., Pouchelet, M., and Boireau, P, (2000). On the track of a human circulating mesenchymal stem cell of neural crest origin. Biomed and Pharmacother. 54, 146-162.

Laywell, E. D., Rakic, P., Kukek6v, V. G., Holland, E. C., and Steindler, D. A. (2000). Identification of a multipotent astrocytic stem cell in the immature and adult mouse brain. Proc. Natl. Acad. Sci. USA 97, 13883-13888.

Lee, J. E., Hollenberg, S. M., Snider, L. Turner, D. L., Lippnick, N., and Weintraub, H. (1995). Conversion of Xenopus ectoderm into neurons by NeuroD, a basic helix-loop-helix protein. Science 268, 836-844.

Lee, J. E. (1997). NeuroD and neurogenesis. Dev. Neurosci. 19, 27-32.

Lois, C., and Alvarez-Buylla, A. (1993). Proliferating subventricular zone cells in the adult mammalian forebrain can differentiate into neurons and glia. Proc. Natl. Acad. Sci. USA 90, 2074-2077.

McKay, R. (1997). Stem cells in the central nervous system. Science 276, 66-71.

Menezes, J. R., and Luskin, M. B. (1994). Expression of neuron-specific tubulin defines a novel population in the proliferative layers of the developing telencephalon. J. Neurosci. 14, 5 399-5416.

Mezey, E., Chandross, K. J., Harta, G., Maki, R. A., and McKercher, S. R. (2000). Turning blood into brain: cells bearing neuronal antigens generated in vivo from bone marrow. Science 290, 1779-1782.

Minturn, J. E., Fryer, H. J., Geschwind, D. H., and Hockfield, S. (1995). TOAD-64, a gene expressed in early neuronal differentiation in the rat, is related to unc-33, a C. elegans gene involved in axon outgrowth. J. Neurosci. 15, 6757-6766.

Morrison, S. J. (2001). Stem cell potential: can anything make anything? Curr. Biol. 11, R7-R9.

Morrow, E. M., Furukawa, T., Lee, J. E., and Cepko, C. L. (1999). NeuroD regulates multiple functions in the developing neural retina in rodent. Development 126, 23-36.

Morshead, C. M., Reynolds, B. A., Craig, C. G., McBumey, M. W., Staines, W. A., Morassutti, D., Weiss, S., and van der Kooy, D. (1994). Neural stem cells in the adult mammalian forebrain: a relatively quiescent subpopulation of subependymal cells. Neuron 13, 1071-1082.

Mukai, T., Yatsuki, H., Masuko, S., Arai, Y., Joh, K., and Hori, K. (199 1). The structure of the brain-specific rat' aldolase C gene and its regional expression. Biochem. Biophys. Res. Comm. 31, 1035-1042.

Owen, M. (1988). Marrow Stromal Stem Cells. J. Cell Sci. Suppl. 10, 63-76.

Parnas, D., and Linial, A (1995). Cholinergic protperties of neurons differentiated frarn an embryonal carcinoma cell line (P19). Int. J. Dev. Neurosci. 13, 767-781.

Reynolds, B.,A., and Weiss, S. (1992). Generation of neurons and astrocytes from isolated cells of the adult mammalian nervous system. Science 255, 1707.

Rickard, D. J., Kassem, M., Hefferan, T. E., Sarkar, G., Spelsberg, T. C., and Riggs, B. L. (1996). Isolation and characterization of osteoblast precursor cells from human bone marrow. J. Bone Mineral. Res. 11, 312-324.

Sanchez-Ramos, J., Song, S., Cardozo-Pelaez, F., Hazzi, C., Stedeford, T., Willing, A., Freeman, T. B., Saporta, S., Janssen, W., Patel, N., Cooper, D. R., and Sanberg, P. R. (2000). Adult bone marrow stromal cells differentiate into neural cells in vitro. Exp. Neurol. 164, 247-256.

Seshi, B., Kumar, S., and Sellers, D. (2000). Human bone marrow stromal cell, Coexpression of markers specific for multiple mesenchymal cell lineages. Blood Cells, Molecules, and Disease 26, 234-246.

Shivers, B. D., Hilbich, C., Multhaup, G., Salbaum, M., Beyreuther, K., and Seeburg, P. H. (1989). Alzheimer's disease amyloidogenic glycoprotein, expression pattern in rat brain suggests a role in cell contact. EMBO J. 7, 13651370.

Smith, W. C., and Harland, R. M. (1992). Expression cloning of noggin, a new dorsalizing factor localized to the Spernann organizer in *Xenopus mesoderm*. Cell 70, 829-840.

Wei, G., Schubiger, G., Harder, F., and Muller, A. M. (2000). Stem cell plasticity in mammals and transdetermination in Drosophila: common themes? Stem Cells 18, 409-414.

Woodbury, D., Schwarz, E. J., Prockop, D T, and Black, I. B. (2000). Adult rat and human bone marrow stromal cells differentiate into neurons. I Neurosci. Res. 6 1, 364-371.

Young, R. H., Butler, D. L., Weber, W., Caplan, A. I., Gordon, S. L., and Fink, D. J. (1998). Use of mesenchymal stem cells in a collagen matrix for Achilles tendon repair. J. Ortho. Res. 6,406.

---

What is claimed is:

1. A method of inducing differentiation of an isolated marrow stromal cell into an insulin secreting pancreatic islet cell comprising contacting an isolated rat or human marrow stromal cell that is positive for cell surface markers CD44, CD71, and CD90 and negative for cell surface markers CD11b and CD45 with at least one antioxidant, thereby inducing differentiation of said rat or human isolated marrow stromal cell into an endodermal/neuronal precursor cell and contacting said endodermal/neuronal precursor cell with basic fibroblast growth factor thereby inducing differentiation of an isolated marrow stromal cell into an insulin secreting pancreatic islet cell.

2. A method of producing an isolated insulin secreting pancreatic islet cell comprising isolating a rat or human marrow stromal cell that is positive for cell surface markers CD44, CD71, and CD90 and negative for cell surface markers CD11b and CD45, contacting said isolated rat or human marrow stromal cell with at least one antioxidant, thereby inducing differentiation of said isolated marrow stromal cell into an endodermal/neuronal precursor cell and contacting said endodermal/neuronal precursor cell with basic fibroblast growth factor thereby producing an insulin secreting pancreatic islet cell.

* * * * *